United States Patent
Thornbrue et al.

(10) Patent No.: US 9,694,267 B1
(45) Date of Patent: Jul. 4, 2017

(54) SWING ANALYSIS METHOD USING A SWING PLANE REFERENCE FRAME

(71) Applicant: Blast Motion Inc., Carlsbad, CA (US)

(72) Inventors: James Thornbrue, San Diego, CA (US); Patrick Cherveny, San Marcos, CA (US)

(73) Assignee: Blast Motion Inc., Carlsbad, CA (US)

( * ) Notice: Subject to any disclaimer, the term of this patent is extended or adjusted under 35 U.S.C. 154(b) by 3 days.

(21) Appl. No.: 15/214,339

(22) Filed: Jul. 19, 2016

(51) Int. Cl.
A63B 69/36 (2006.01)
A63B 69/00 (2006.01)

(52) U.S. Cl.
CPC .. A63B 69/0002 (2013.01); A63B 2069/0008 (2013.01)

(58) Field of Classification Search
USPC .......... 473/221–223, 257, 453, 409
See application file for complete search history.

(56) References Cited

U.S. PATENT DOCUMENTS

| | | |
|---|---|---|
| 1,712,537 A | 5/1929 | White |
| 3,182,508 A | 5/1965 | Varju |
| 3,226,704 A | 12/1965 | Petrash |
| 3,270,564 A | 9/1966 | Evans |
| 3,788,647 A | 1/1974 | Evans |
| 3,792,863 A | 2/1974 | Evans |
| 3,806,131 A | 4/1974 | Evans |
| 3,945,646 A | 3/1976 | Hammond |
| 4,759,219 A | 7/1988 | Cobb et al. |
| 4,898,389 A | 2/1990 | Plutt |
| 4,902,014 A | 2/1990 | Bontomase et al. |

(Continued)

FOREIGN PATENT DOCUMENTS

| | | |
|---|---|---|
| EP | 2025369 A2 | 2/2009 |
| JP | 2004207985 | 7/2004 |

(Continued)

OTHER PUBLICATIONS

International Search Report received for PCT Application No. PCT/US2012/065716, dated Jan. 3, 2013, 10 pages.

(Continued)

*Primary Examiner* — Nini Legesse
(74) *Attorney, Agent, or Firm* — Arc IP Law, PC; Joseph J. Mayo

(57) ABSTRACT

A method for analyzing sensor data from baseball swings (or swings in similar sports) that transforms data into a reference frame defined by the bat orientation and velocity at impact. The swing plane defined by these two axes provides a natural and robust reference frame for physically relevant measurements of swing characteristics. Illustrative swing metrics derived from swing plane reference frame data include: swing speed, defined as a rotational rate within the swing plane; total swing angle, defined as the angular change within the swing plane; and swing tempo, defined as the percentage of peak swing speed achieved halfway through the swing. Analyzing these metrics from multiple swings across multiple users identifies factors that contribute to peak performance. Metrics may be combined into multidimensional feature vectors that characterize a swing; these feature vectors may be used to group swings into swing styles or to match swings against similar players.

23 Claims, 13 Drawing Sheets

(56) References Cited

U.S. PATENT DOCUMENTS

| | | |
|---|---|---|
| 4,910,677 A | 3/1990 | Remedio et al. |
| 4,940,236 A | 7/1990 | Allen |
| 4,991,850 A | 2/1991 | Wilhlem |
| 5,056,783 A | 10/1991 | Matcovich et al. |
| 5,086,390 A | 2/1992 | Matthews |
| 5,111,410 A | 5/1992 | Nakayama et al. |
| 5,127,044 A | 6/1992 | Bonito et al. |
| 5,184,295 A | 2/1993 | Mann |
| 5,230,512 A | 7/1993 | Tattershall |
| 5,233,544 A | 8/1993 | Kobayashi |
| 5,249,967 A | 10/1993 | O'Leary et al. |
| 5,259,620 A | 11/1993 | Marocco |
| 5,283,733 A | 2/1994 | Colley |
| 5,298,904 A | 3/1994 | Olich |
| 5,332,225 A | 7/1994 | Ura |
| 5,333,061 A | 7/1994 | Nakashima et al. |
| 5,364,093 A | 11/1994 | Huston et al. |
| 5,372,365 A | 12/1994 | McTeigue et al. |
| 5,441,256 A | 8/1995 | Hackman |
| 5,441,269 A | 8/1995 | Henwood |
| 5,443,260 A | 8/1995 | Stewart et al. |
| 5,486,001 A | 1/1996 | Baker |
| 5,524,081 A | 6/1996 | Paul |
| 5,542,676 A | 8/1996 | Howe et al. |
| 5,592,401 A | 1/1997 | Kramer |
| 5,610,590 A | 3/1997 | Johnson et al. |
| 5,638,300 A | 6/1997 | Johnson |
| 5,665,006 A | 9/1997 | Pellegrini |
| 5,688,183 A | 11/1997 | Sabatino et al. |
| 5,694,340 A | 12/1997 | Kim |
| 5,772,522 A | 6/1998 | Nesbit |
| 5,779,555 A | 7/1998 | Nomura et al. |
| 5,792,001 A | 8/1998 | Henwood |
| 5,819,206 A | 10/1998 | Horton |
| 5,826,578 A | 10/1998 | Curchod |
| 5,868,578 A | 2/1999 | Baum |
| 5,904,484 A | 5/1999 | Burns |
| 5,941,779 A | 8/1999 | Zeiner-Gundersen |
| 5,973,596 A | 10/1999 | French et al. |
| 5,998,968 A | 12/1999 | Pittman et al. |
| 6,012,995 A | 1/2000 | Martin |
| 6,030,109 A | 2/2000 | Lobsenz |
| 6,044,704 A | 4/2000 | Sacher |
| 6,073,086 A | 6/2000 | Marinelli |
| 6,224,493 B1 | 5/2001 | Lee et al. |
| 6,248,021 B1 | 6/2001 | Ognjanovic |
| 6,253,159 B1 | 6/2001 | Bett et al. |
| 6,254,492 B1 | 7/2001 | Taggett |
| 6,266,623 B1 | 7/2001 | Vock et al. |
| 6,293,802 B1 | 9/2001 | Ahlgren |
| 6,366,205 B1 | 4/2002 | Sutphen |
| 6,441,745 B1 | 8/2002 | Gates |
| 6,456,938 B1 | 9/2002 | Barnard |
| 6,537,076 B2 | 3/2003 | McNitt |
| 6,540,620 B1 | 4/2003 | Consiglio |
| 6,567,536 B2 | 5/2003 | McNitt |
| 6,582,328 B2 | 6/2003 | Kuta et al. |
| 6,611,141 B1 | 8/2003 | Schulz |
| 6,697,820 B1 | 2/2004 | Tarlie |
| 6,705,942 B1 | 3/2004 | Crook et al. |
| 6,746,336 B1 | 6/2004 | Brant et al. |
| 6,757,572 B1 | 6/2004 | Forest |
| 6,774,932 B1 | 8/2004 | Ewing et al. |
| 6,802,772 B1 | 10/2004 | Kunzle et al. |
| 6,868,338 B1 | 3/2005 | Elliott |
| 6,900,759 B1 | 5/2005 | Katayama |
| 6,908,404 B1 | 6/2005 | Gard |
| 6,923,729 B2 | 8/2005 | McGinty et al. |
| 7,004,848 B2 | 2/2006 | Konow |
| 7,021,140 B2 | 4/2006 | Perkins |
| 7,034,694 B2 | 4/2006 | Yamaguchi et al. |
| 7,037,198 B2 | 5/2006 | Hameen-Anttila |
| 7,092,846 B2 | 8/2006 | Vock et al. |
| 7,118,498 B2 | 10/2006 | Meadows et al. |
| 7,121,962 B2 | 10/2006 | Reeves |
| 7,143,639 B2 | 12/2006 | Gobush |
| 7,160,200 B2 | 1/2007 | Grober |
| 7,175,177 B2 | 2/2007 | Meifu et al. |
| 7,205,894 B1 | 4/2007 | Savage |
| 7,212,943 B2 | 5/2007 | Aoshima et |
| 7,219,033 B2 | 5/2007 | Kolen |
| 7,234,351 B2 | 6/2007 | Perkins |
| 7,264,554 B2 | 9/2007 | Bentley |
| 7,283,647 B2 | 10/2007 | McNitt |
| 7,421,369 B2 | 9/2008 | Clarkson |
| 7,433,805 B2 | 10/2008 | Vock et al. |
| 7,457,439 B1 | 11/2008 | Madsen |
| 7,457,724 B2 | 11/2008 | Vock et al. |
| 7,492,367 B2 | 2/2009 | Mahajan et al. |
| 7,494,236 B2 | 2/2009 | Lim |
| 7,499,828 B2 | 3/2009 | Barton |
| 7,561,989 B2 | 7/2009 | Banks |
| 7,623,987 B2 | 11/2009 | Vock et al. |
| 7,627,451 B2 | 12/2009 | Vock et al. |
| 7,689,378 B2 | 3/2010 | Kolen |
| 7,713,148 B2 | 5/2010 | Sweeney |
| 7,736,242 B2 | 6/2010 | Stites et al. |
| 7,771,263 B2 | 8/2010 | Telford |
| 7,780,450 B2 | 8/2010 | Tarry |
| 7,800,480 B1 | 9/2010 | Joseph et al. |
| 7,813,887 B2 | 10/2010 | Vock et al. |
| 7,831,212 B1 | 11/2010 | Balardeta et al. |
| 7,871,333 B1 | 1/2011 | Davenport |
| 7,966,154 B2 | 6/2011 | Vock et al. |
| 7,983,876 B2 | 7/2011 | Vock et al. |
| 8,036,826 B2 | 10/2011 | MacIntosh et al. |
| 8,117,888 B2 | 2/2012 | Chan et al. |
| 8,172,722 B2 | 5/2012 | Molyneux et al. |
| 8,231,506 B2 | 7/2012 | Molyneux et al. |
| 8,249,831 B2 | 8/2012 | Vock et al. |
| 8,257,191 B2 | 9/2012 | Stites et al. |
| 8,282,487 B2 | 10/2012 | Wilson et al. |
| 8,314,840 B1 | 11/2012 | Funk |
| 8,352,211 B2 | 1/2013 | Vock et al. |
| 8,400,548 B2 | 3/2013 | Bilbrey et al. |
| 8,425,292 B2 | 4/2013 | Lui et al. |
| 8,527,228 B2 | 9/2013 | Panagas |
| 8,565,483 B2 | 10/2013 | Nakaoka |
| 8,696,482 B1 * | 4/2014 | Pedenko ............ A63B 69/3632 473/221 |
| 8,723,986 B1 | 5/2014 | Merrill |
| 8,725,452 B2 | 5/2014 | Han |
| 8,764,576 B2 | 7/2014 | Takasugi |
| 8,781,610 B2 | 7/2014 | Han |
| 8,876,621 B2 | 11/2014 | Shibuya |
| 8,888,603 B2 | 11/2014 | Sato et al. |
| 8,929,709 B2 | 1/2015 | Lokshin |
| 8,944,932 B2 | 2/2015 | Sato et al. |
| 8,956,238 B2 | 2/2015 | Boyd et al. |
| 8,988,341 B2 | 3/2015 | Lin et al. |
| 8,989,441 B2 | 3/2015 | Han et al. |
| 9,060,682 B2 | 6/2015 | Lokshin |
| 9,146,134 B2 | 9/2015 | Lokshin et al. |
| 2001/0029207 A1 | 10/2001 | Cameron et al. |
| 2001/0035880 A1 | 11/2001 | Musatov et al. |
| 2001/0045904 A1 | 11/2001 | Silzer, Jr. |
| 2001/0049636 A1 | 12/2001 | Hudda et al. |
| 2002/0004723 A1 | 1/2002 | Meifu et al. |
| 2002/0019677 A1 | 2/2002 | Lee |
| 2002/0049507 A1 | 4/2002 | Hameen-Anttila |
| 2002/0052750 A1 | 5/2002 | Hirooka |
| 2002/0064764 A1 | 5/2002 | Fishman |
| 2002/0072815 A1 | 6/2002 | McDonough et al. |
| 2002/0077189 A1 | 6/2002 | Tuer et al. |
| 2002/0082775 A1 | 6/2002 | Meadows et al. |
| 2002/0115046 A1 | 8/2002 | McNitt et al. |
| 2002/0126157 A1 | 9/2002 | Farago et al. |
| 2002/0151994 A1 | 10/2002 | Sisco |
| 2002/0173364 A1 | 11/2002 | Boscha |
| 2002/0177490 A1 | 11/2002 | Yong et al. |
| 2002/0188359 A1 | 12/2002 | Morse |
| 2003/0008722 A1 | 1/2003 | Konow |
| 2003/0073518 A1 | 4/2003 | Marty |
| 2003/0074659 A1 | 4/2003 | Louzoun |

(56) References Cited

U.S. PATENT DOCUMENTS

| | | |
|---|---|---|
| 2003/0109322 A1 | 6/2003 | Funk et al. |
| 2003/0191547 A1 | 10/2003 | Morse |
| 2003/0208830 A1 | 11/2003 | Marmaropoulos |
| 2004/0028258 A1 | 2/2004 | Naimark et al. |
| 2004/0033843 A1 | 2/2004 | Miller |
| 2004/0044493 A1 | 3/2004 | Coulthard |
| 2004/0147329 A1 | 7/2004 | Meadows et al. |
| 2004/0227676 A1 | 11/2004 | Kim et al. |
| 2004/0248676 A1 | 12/2004 | Taylor |
| 2005/0021292 A1 | 1/2005 | Vock et al. |
| 2005/0023763 A1 | 2/2005 | Richardson |
| 2005/0032582 A1 | 2/2005 | Mahajan et al. |
| 2005/0054457 A1 | 3/2005 | Eyestone et al. |
| 2005/0156068 A1 | 7/2005 | Ivans |
| 2005/0203430 A1 | 9/2005 | Williams et al. |
| 2005/0213076 A1 | 9/2005 | Saegusa |
| 2005/0215340 A1 | 9/2005 | Stites et al. |
| 2005/0227775 A1 | 10/2005 | Cassady et al. |
| 2005/0261073 A1 | 11/2005 | Farrington, Jr. et al. |
| 2005/0268704 A1 | 12/2005 | Bissonnette et al. |
| 2005/0272516 A1 | 12/2005 | Gobush |
| 2005/0282650 A1 | 12/2005 | Miettinen et al. |
| 2005/0288119 A1 | 12/2005 | Wang et al. |
| 2006/0020177 A1 | 1/2006 | Seo et al. |
| 2006/0025229 A1 | 2/2006 | Mahajan et al. |
| 2006/0038657 A1 | 2/2006 | Denison et al. |
| 2006/0063600 A1 | 3/2006 | Grober |
| 2006/0068928 A1 | 3/2006 | Nagy |
| 2006/0084516 A1 | 4/2006 | Eyestone et al. |
| 2006/0109116 A1 | 5/2006 | Keays |
| 2006/0122002 A1 | 6/2006 | Konow |
| 2006/0166738 A1 | 7/2006 | Eyestone et al. |
| 2006/0189389 A1 | 8/2006 | Hunter et al. |
| 2006/0199659 A1 | 9/2006 | Caldwell |
| 2006/0250745 A1 | 11/2006 | Butler et al. |
| 2006/0270450 A1 | 11/2006 | Garratt et al. |
| 2006/0276256 A1 | 12/2006 | Storek |
| 2006/0284979 A1 | 12/2006 | Clarkson |
| 2007/0052807 A1 | 3/2007 | Zhou et al. |
| 2007/0062284 A1 | 3/2007 | Machida |
| 2007/0081695 A1 | 4/2007 | Foxlin et al. |
| 2007/0087866 A1 | 4/2007 | Meadows et al. |
| 2007/0099715 A1 | 5/2007 | Jones et al. |
| 2007/0111811 A1 | 5/2007 | Grober |
| 2007/0129178 A1 | 6/2007 | Reeves |
| 2007/0135225 A1 | 6/2007 | Nieminen |
| 2007/0135237 A1 | 6/2007 | Reeves |
| 2007/0219744 A1 | 9/2007 | Kolen |
| 2007/0265105 A1 | 11/2007 | Barton |
| 2007/0270214 A1 | 11/2007 | Bentley |
| 2007/0298896 A1 | 12/2007 | Nusbaum |
| 2008/0027502 A1 | 1/2008 | Ransom |
| 2008/0085778 A1 | 4/2008 | Dugan |
| 2008/0090703 A1 | 4/2008 | Rosenberg |
| 2008/0108456 A1 | 5/2008 | Bonito |
| 2008/0164999 A1 | 7/2008 | Otto |
| 2008/0190202 A1 | 8/2008 | Kulach et al. |
| 2008/0234935 A1 | 9/2008 | Wolf et al. |
| 2008/0280642 A1 | 11/2008 | Coxhill et al. |
| 2008/0284979 A1 | 11/2008 | Yee et al. |
| 2008/0285805 A1 | 11/2008 | Luinge et al. |
| 2009/0002316 A1 | 1/2009 | Rofougaran |
| 2009/0017944 A1 | 1/2009 | Savarese et al. |
| 2009/0029754 A1 | 1/2009 | Slocum et al. |
| 2009/0033741 A1 | 2/2009 | Oh et al. |
| 2009/0036237 A1 | 2/2009 | Nipper et al. |
| 2009/0048044 A1 | 2/2009 | Oleson et al. |
| 2009/0055820 A1 | 2/2009 | Huang |
| 2009/0088276 A1 | 4/2009 | Solheim et al. |
| 2009/0111602 A1 | 4/2009 | Savarese et al. |
| 2009/0131190 A1 | 5/2009 | Kimber |
| 2009/0137333 A1 | 5/2009 | Lin et al. |
| 2009/0174676 A1 | 7/2009 | Westerman |
| 2009/0177097 A1 | 7/2009 | Ma et al. |
| 2009/0191846 A1 | 7/2009 | Shi |
| 2009/0209343 A1 | 8/2009 | Foxlin et al. |
| 2009/0209358 A1 | 8/2009 | Niegowski |
| 2009/0213134 A1 | 8/2009 | Stephanick et al. |
| 2009/0222163 A1 | 9/2009 | Plante |
| 2009/0233735 A1 | 9/2009 | Savarese et al. |
| 2009/0254971 A1 | 10/2009 | Herz et al. |
| 2009/0299232 A1 | 12/2009 | Lanfermann et al. |
| 2010/0049468 A1 | 2/2010 | Papadourakis |
| 2010/0062869 A1 | 3/2010 | Chung et al. |
| 2010/0063778 A1 | 3/2010 | Schrock et al. |
| 2010/0063779 A1 | 3/2010 | Schrock et al. |
| 2010/0091112 A1 | 4/2010 | Veeser et al. |
| 2010/0093458 A1 | 4/2010 | Davenport et al. |
| 2010/0099509 A1 | 4/2010 | Ahem et al. |
| 2010/0103269 A1 | 4/2010 | Wilson et al. |
| 2010/0113174 A1 | 5/2010 | Ahern |
| 2010/0121227 A1 | 5/2010 | Stirling et al. |
| 2010/0121228 A1 | 5/2010 | Stirling et al. |
| 2010/0130298 A1 | 5/2010 | Dugan et al. |
| 2010/0144414 A1 | 6/2010 | Edis et al. |
| 2010/0144456 A1 | 6/2010 | Ahern |
| 2010/0204616 A1 | 8/2010 | Shears et al. |
| 2010/0216564 A1 | 8/2010 | Stites et al. |
| 2010/0222152 A1 | 9/2010 | Jaekel et al. |
| 2010/0308105 A1 | 12/2010 | Savarese et al. |
| 2010/0323794 A1 | 12/2010 | Su |
| 2011/0029235 A1 | 2/2011 | Berry |
| 2011/0037778 A1 | 2/2011 | Deng et al. |
| 2011/0050864 A1 | 3/2011 | Bond |
| 2011/0052005 A1 | 3/2011 | Selner |
| 2011/0053688 A1 | 3/2011 | Crawford |
| 2011/0075341 A1 | 3/2011 | Lau et al. |
| 2011/0081981 A1 | 4/2011 | Okamoto |
| 2011/0126184 A1 | 5/2011 | Lisboa |
| 2011/0165998 A1 | 7/2011 | Lau et al. |
| 2011/0195780 A1 | 8/2011 | Lu |
| 2011/0230273 A1 | 9/2011 | Niegowski et al. |
| 2011/0230274 A1 | 9/2011 | Lafortune et al. |
| 2011/0230985 A1 | 9/2011 | Niegowski et al. |
| 2011/0230986 A1 | 9/2011 | Lafortune |
| 2011/0238308 A1 | 9/2011 | Miller et al. |
| 2011/0305369 A1 | 12/2011 | Bentley |
| 2012/0023354 A1 | 1/2012 | Chino |
| 2012/0052972 A1 | 3/2012 | Bentley |
| 2012/0115626 A1* | 5/2012 | Davenport ......... A63B 24/0006 473/223 |
| 2012/0115682 A1 | 5/2012 | Homsi |
| 2012/0116548 A1 | 5/2012 | Goree et al. |
| 2012/0120572 A1 | 5/2012 | Bentley |
| 2012/0157241 A1* | 6/2012 | Nomura ............. A63B 69/0002 473/422 |
| 2012/0179418 A1 | 7/2012 | Takasugi et al. |
| 2012/0191405 A1 | 7/2012 | Molyneux et al. |
| 2012/0295726 A1* | 11/2012 | Cherbini ............ G09B 19/0038 473/222 |
| 2012/0316004 A1 | 12/2012 | Shibuya |
| 2013/0029791 A1* | 1/2013 | Rose .................. G09B 19/0038 473/409 |
| 2013/0095941 A1 | 4/2013 | Bentley et al. |
| 2013/0110415 A1 | 5/2013 | Davis et al. |
| 2013/0128022 A1 | 5/2013 | Bose et al. |
| 2013/0173212 A1 | 7/2013 | Saiki et al. |
| 2013/0178304 A1 | 7/2013 | Chan |
| 2013/0191063 A1 | 7/2013 | Nomura |
| 2013/0225309 A1 | 8/2013 | Bentley et al. |
| 2013/0271602 A1 | 10/2013 | Bentley et al. |
| 2013/0298668 A1 | 11/2013 | Sato |
| 2013/0319113 A1 | 12/2013 | Mizuta |
| 2013/0330054 A1 | 12/2013 | Lokshin |
| 2013/0332004 A1 | 12/2013 | Gompert et al. |
| 2013/0346013 A1 | 12/2013 | Lokshin |
| 2014/0019083 A1 | 1/2014 | Nakaoka |
| 2014/0100048 A1 | 4/2014 | Ota et al. |
| 2014/0100049 A1 | 4/2014 | Ota et al. |
| 2014/0100050 A1 | 4/2014 | Ota et al. |
| 2014/0135139 A1* | 5/2014 | Shibuya ............. A63B 24/0006 473/207 |
| 2014/0156214 A1 | 6/2014 | Nomura |
| 2014/0172873 A1 | 6/2014 | Varoglu et al. |

(56) References Cited

U.S. PATENT DOCUMENTS

| | | | |
|---|---|---|---|
| 2014/0200094 A1* | 7/2014 | Parke | A63F 13/00 473/223 |
| 2014/0229135 A1 | 8/2014 | Nomura | |
| 2014/0229138 A1 | 8/2014 | Goree et al. | |
| 2014/0257743 A1 | 9/2014 | Lokshin et al. | |
| 2014/0257744 A1 | 9/2014 | Lokshin et al. | |
| 2014/0295982 A1 | 10/2014 | Shibuya | |
| 2014/0376876 A1 | 12/2014 | Bentley et al. | |
| 2014/0378239 A1 | 12/2014 | Sato et al. | |
| 2014/0379293 A1 | 12/2014 | Sato | |
| 2014/0379294 A1 | 12/2014 | Shibuya et al. | |
| 2014/0379295 A1 | 12/2014 | Sato et al. | |
| 2015/0007658 A1 | 1/2015 | Ishikawa et al. | |
| 2015/0012240 A1 | 1/2015 | Sato | |
| 2015/0042481 A1 | 2/2015 | Nomura | |
| 2015/0098688 A1 | 4/2015 | Lokshin | |
| 2015/0154452 A1 | 6/2015 | Bentley et al. | |
| 2015/0256689 A1 | 9/2015 | Erkkila et al. | |
| 2015/0348591 A1 | 12/2015 | Kaps et al. | |

FOREIGN PATENT DOCUMENTS

| | | |
|---|---|---|
| JP | 2011000367 | 6/2011 |
| JP | 2012196241 | 10/2012 |
| KR | 10-20030085275 | 11/2003 |
| KR | 10-2006-0041060 | 5/2006 |
| KR | 10-2007-0119018 | 12/2007 |
| KR | 10-20100020131 | 2/2010 |
| KR | 10-20100074068 | 7/2010 |
| KR | 10-1079319 | 6/2011 |
| WO | 94/27683 | 8/1994 |
| WO | 2011057194 | 5/2011 |
| WO | 2014085744 | 6/2014 |

OTHER PUBLICATIONS myCaddie, 2009, retrieved on Sep. 26, 2012 from http://www.iMakePars.com, 4 pages.
Swing it See it Fix it, Improve Gold Swing, SwingSmart Golf Analyzer, retrieved on Sep. 26, 2012 from http://www.SwingSmart.com, 2 pages.
Learn how Swingbyte can improve your game, retrieved on Sep. 26, 2012 from http://www.swingbyte.com, 2 pages.
International Search Report received for PCT Application No. PCT/US2011/055173, Mar. 6, 2012, 8 pages.
International Search Report received for PCT Application No. PCT/US2011/049461, Feb. 23, 2012, 14 pages, 2012.
PCT Search Report, PCT/US2012/029310, dated Sep. 28, 2012, 3 pages.
IPRP, PCT/US2011/049461, dated Mar. 7, 2013, 6 pages.
IPRP, PCT/US2011/058182, dated Apr. 30, 2013, 5 pages.
IPER, PCT/US2011/055173, dated Apr. 25, 2013, 5 pages, (2013).
IPRP, PCT/US2012/065716, dated May 20, 2014, 6 pages.
International Search Report for PCT Application No. PCT/US2013/021999, dated Apr. 30, 2013, 8 pages.
International Search Report for PCT Application No. PCT/US2012/066915, dated Mar. 29, 2013, 10 pages.
International Search Report for PCT Application No. PCT/US2015/26896, dated Jul. 28, 2015, 15 pages.
International Search Report for PCT Application No. PCTUS2015/26917, dated Jul. 30, 2015, 16 pages.
The Nike+FuelBand User's Guide, rev 14, 26 pages, 2012.
UP by Jawbone Extended User Guide, 10 pages, 2012.
Armour39, Under Armour Guarantee, Getting Started, retrieved from the Internet on Jul. 12, 2013, 7 pages.
Armour39 Module & Chest Strap, retrieved from the Internet on Jul. 12, 2013, 6 pages.
miCoach Pacer User Manual, 31 pages, (2009).
Foreman et al. "A Comparative Analysis for the Measurement of Head Accelerations in Ice Hockey Helmets using Non-Accelerometer Based Systems," Nov. 19, 2012, 13 pages.
Reebok—CCM and MC10 to Launch Revolutionary Sports Impact Indicator, MC10 News (http://www.mc10inc.com/news/), Oct. 24, 2012, 3 pages.
CheckLight MC10 Overview, Reebok International Limited, Nov. 20, 2012, 7 pages.
Reebok and MC10 Team Up to Build CheckLight, a Head Impact Indicator (Hands-on), MC10 News (http://www.mc10inc.com/news/), Jan. 11, 2013, 1 pg.
TRACE—The Most Advanced Activity Monitor for Action Sports, webpage, retrieved on Aug. 6, 2013, 22 pages.
CheckLight, Sports/Activity Impact Indicator, User Manual, 13 pages, 2013, Reebok International Limited.
King, The Design and Application of Wireless Mems Inertial Measurement Units for the Measurement and Analysis of Golf Swings, 2008.
Grober, An Accelerometer Based Instrumentation of the Golf Club: Comparative Analysis of Golf Swings, 2009.
Gehrig et al, Visual Golf Club Tracking for Enhanced Swing Analysis, Computer Vision Lab, Lausanne, Switzerland, 2003.
Pocketpro Golf Designs, PocketPro Full Swing Analysis in Your Pocket, www.PocketPro.org, (2011).
Clemson University, Golf Shot Tutorial, http://www.webnucleo.org/home/online_tools/newton/0.4/html/about_this_tool/tutorials/golf_1.shp.cgi, retrieved on Nov. 10, 2011.
miCoach SPEED_CELL TM, User Manual, 23 pages, (2011).
Nike+iPod, User Guide, 32 pages (2010).
SureShotGPS SS9000X, Intelligent Touch, Instruction Manual, 25 page, 2011.
ActiveReplay, "TRACE—The Most Advanced Activity Monitor for Action Spoils", http://www.kickstarter.com/projects/activereplay/trace-the-most-advanced-activity-monitor-for-actio, 13 pages, Oct. 1, 2013.
ZEPP Golfsense@Launch2011, https://www.youtube.com/watch?v=VnOcu8sziIk (video), Mar. 14, 2011.
Epson US Newsroom, "Epson America Enters Sports Wearables Market with Introduction of M-Tracer MT500GII Golf Swing Analyzer", www.news.epson.com, Jan. 5, 2015, 4 pages.
International Search Report and Written Opinion dated Dec. 22, 2015 received in PCTUS1561695, 7 pages.
Search Report Received in PCT2013021999 dated Jan. 21, 2016.
Patent Examination Report received in Australia Application No. 2011313952, dated Mar. 15, 2016, 5 pages.
"About Banjo" webpages retrieved from internet, dated 2015.
International Search Report and Written Opinion mailed in PCTUS1642674 on Aug. 12, 2016, 9 pages.
International Search Report received in PCT/US2016/042668, dated Oct. 4, 2016, 21 pages.
International Search Report received in PCT/US2016/042671, dated Oct. 13, 2016, 17 pages.
*Zepp Labs, Inc.* v. *Blast Motion, Inc.* Petition for Inter Partes Review of U.S. Pat. No. 8,903,521 filed on Feb. 24, 2016, as IPR2016-00672, and accompanying Declaration of Dr. Steven M. Nesbit.
*Zepp Labs, Inc.* v. *Blast Motion, Inc.* Petition for Inter Partes Review of U.S. Pat. No. 9,039,527 filed on Feb. 24, 2016, as IPR2016-00674, and accompanying Declaration of Dr. Steven M. Nesbit.
*Zepp Labs, Inc.* v. *Blast Motion, Inc.* Petition for Inter Partes Review of U.S. Pat. No. 8,941,723 filed on Feb. 24, 2016, as IPR2016-00675, and accompanying Declaration of Dr. Steven M. Nesbit.
*Zepp Labs, Inc.* v. *Blast Motion, Inc.* Petition for Inter Partes Review of U.S. Pat. No. 8,905,855 filed on Feb. 24, 2016, as IPR2016-00676, and accompanying Declaration of Dr. Steven M. Nesbit.
*Zepp Labs, Inc.* v. *Blast Motion, Inc.* Petition for Inter Partes Review of U.S. Pat. No. 8,944,928 filed on Feb. 24, 2016, as IPR2016-00677, and accompanying Declaration of Dr. Steven M. Nesbit.
Chris Otto, et al, "System Architecture of a Wireless Body Area Sensor Network for Ubiquitous Health Monitoring", *Journal of Mobile Multimedia*, vol. 1, No. 4, Jan. 10, 2006, University of Alabama in Huntsville, 20 Pages.
Linx Technologies "High Performance RF Module: Hp3 Series Transmitter Module Data Guide Description", Jul. 27, 2011, 13 pages.

(56) References Cited

OTHER PUBLICATIONS

Roger Allan, "Wireless Sensor Architectures Uses Bluetooth Standard", www.electronicdesign.com/communications/wireless-sensor-architecture-uses-bluetooth-standard, Aug. 7, 2000, 5 pages.

Don Tuite, "Motion-Sensing MEMS Gyros and Accelerometers are Everywhere", www.electronicdesign.com/print/analog/motion-sensing-mems-gyros-and-accelerometers-are-everywhere, Jul. 9, 2009, 6 pages.

InvenSense News Release, "InvenSense Unveils World's $1^{st}$ IMU Solution for Consumer Applications", ir.invensense.com, 2016, 2 Pages.

Dean Takahashi, "Facebook, Twitter, Last.fm coming to Xbox Live this Fall", Jun. 1, 2009, Webpage printout, 5 pages.

The iClub System, Products pages, www.iclub.net, 2001-2005, 5 pages.

Websters New College Dictionary, Definition of "Virtual Reality", Third Edition, 2005, 3 Pages.

SmartSwing, "SmartSwing Introduces Affordable Intelligent Golf Club", www.smartswinggolf.com, Jan. 2006, 2 pages.

Henrick Arfwedson, et al., "Ericsson's Bluetooth modules", Ericsson Review No. 4, 1999, 8 pages.

ZigBees, "Zigbee information", www.zigbees.com, 2015, 4 pages.

SolidState Technology, "MEMS enable smart golf clubs", www.electroiq.com, 2005, 3 pages.

IGN, "Japanese WII Price Release Date Revealed", www.ign.com, 2006, 1 page.

First Annual Better Golf Through Technology Conference 2006 webpage, www.bettergolfthroughtechnology.com, Massachusetts Institute of Technology, Cambridge Massachusetts, Feb. 2006, 1 page.

Concept2Rowing, "Training" web content, www.concept2.com, 2009, 1 page.

Expresso, Products pages, www.expresso.com/products, 2009, 2 pages.

Manish Kalia, et al., "Efficient Policies for Increasing Capacity in Bluetooth: An Indoor Pico-Cellular Wireless System", IBM India Research Laboratory, Indian Institute of Technology, 2000, 5 pages.

R. Rao, et al., "Demand-Based Bluetooth Scheduling", Pennsylvania State University, 2001, 13 pages.

International Search Report and Written Opinion received in PCT/US2016/042676, dated Oct. 24, 2016 (12 pages).

International Preliminary Report on Patentability received in PCT/US2015/026917, dated Nov. 3, 2016 (5 pages).

\* cited by examiner

SWING ANALYSIS METHOD USING A SWING PLANE REFERENCE FRAME

BACKGROUND OF THE INVENTION

Field of the Invention

One or more embodiments setting forth the ideas described throughout this disclosure pertain to the field of motion capture sensors and analysis of motion capture data. More particularly, but not by way of limitation, one or more aspects of the invention enable a method for analysis of a baseball swing using data captured from a motion sensor on the bat.

Description of the Related Art

Methods for analyzing baseball swings include video capture systems that record high speed video of a swing and that analyze the motion of the bat and the player from the video. These systems are typically expensive and complex, and they are not portable. Another method is to attach a motion sensor to a bat, and to analyze motion data captured by the sensor during the swing. A significant challenge for these sensor based solutions is interpretation of the sensor data. In particular, sensors typically capture data in a local reference frame defined by the sensor geometry. This sensor reference frame moves and rotates constantly throughout a swing. For baseball in particular, this challenge is more complex since the bat has rotational symmetry around its long axis; thus the batter can hold the bat in multiple orientations while swinging, which changes the sensor data. There are no known methods that transform swing sensor data from a sensor based reference frame to a meaningful reference frame that is insensitive to these changes in orientation. Existing methods emphasize vector magnitudes (such as total swing speed) in defining swing metrics because these magnitudes are invariant to rotations in the sensor reference frame. However, individual components of sensor measurements along carefully chosen transformed axes provide more detailed and more physically meaningful information.

For at least the limitations described above there is a need for a baseball swing analysis method using a swing plane reference frame.

BRIEF SUMMARY OF THE INVENTION

Embodiments of the invention enable a method to analyze a baseball swing by transforming sensor data captured during the swing to a reference frame that reflects the physics and geometry of the swing itself. This reference frame is called a swing plane reference frame. Metrics defined with respect to the swing plane reference frame provide a detailed characterization of a swing; these metrics can be compared across swings to analyze the factors that affect swing performance.

One or more embodiments of the invention may obtain sensor data from a sensor coupled to a bat while the bat is swung to hit or otherwise contact a ball. The bat may be for example, without limitation, a baseball bat, a softball bat, or a cricket bat. The sensor may for example be an inertial motion sensor that includes any or all of a three axis accelerometer, a three axis gyroscope, and a three axis magnetometer. The sensor may be a compound sensor that incorporates multiple individual sensors of any types. A compound sensor may include multiple sensors at different locations on the bat; for example, without limitation, some sensors may be located on the knob of the bat, and other sensors may be located at the tip of the bat. Sensor data may be collected throughout the swing, for example at a rate of 10 Hz, 100 Hz, 1000 Hz, or more. The sensor data may be analyzed to determine the time of impact between the bat and a ball. For example, accelerometer data may detect the shock of the impact. A bat trajectory may be calculated from the sensor data. The trajectory may include motion data samples at multiple points in time throughout the swing; each motion data sample may describe one or more of the bat's position, orientation, velocity, angular velocity, acceleration, or angular acceleration at a point in time.

Analysis of the bat trajectory may include calculating an impact velocity vector for the velocity of the bat at the time of impact with the ball. Using the impact velocity vector, a reference frame called the swing plane reference frame may be defined for the swing. The swing plane reference frame may be formed from three axes: a first axis may be the longitudinal axis of the bat; a second axis may be the impact velocity vector; and a third axis may be orthogonal to the swing plane spanned by the first (bat) axis and the second (impact velocity) axis. The angular velocity vector of the bat, which is the rotational axis that is perpendicular to the bat's instantaneous plane of rotation, may also be used to define or calculate one or more of the axes of the swing plane reference frame. The bat trajectory may then be transformed to the swing plane reference frame for further analysis. This analysis may include creating one or more swing metrics from the transformed bat trajectory.

Illustrative metrics that may be defined using the transformed bat trajectory include the following: Swing plane speed at any point in time during the swing may be defined as an instantaneous rotational speed of the bat trajectory projected onto the swing plane. In one or more embodiments this swing plane speed may be calculated by projecting angular velocity onto the normal vector of the swing plane. Swing duration may then be calculated by defining the start of downswing as the latest time prior to impact when the swing plane speed has magnitude zero. Subtracting the start of downswing from the time of impact generates a duration metric called the time to contact, which measures how quickly the batter responds. The amount of bat motion may be measured as the total angle traversed by the bat both in the swing plane (yielding a metric called total swing angle) and in a plane orthogonal to the swing plane (yielding a different metric called off plane angle). A measure of bat acceleration through the swing may be defined by measuring the swing plane speed at the halfway point of a swing; the ratio of this halfway point swing plane speed to the peak swing plane speed through the swing is defined as the swing tempo metric.

One or more embodiments may obtain a database of swings from multiple players. Analysis of the database may be used to generate one or more performance rating functions that rate swings on their relative performance. These performance rating functions may be applied to rate future swings, and to provide feedback to users on the performance and characteristics of their swings. Metrics and other data associated with swings in the database may be combined into feature vectors that may be used for classification and matching algorithms. For example, analysis of the database may be used to group swings into swing styles, where swings associated with the same swing style have similar feature vectors. Feature vector clustering and matching may be used to provide feedback to a user on the style of his or her swing, and to identify other users with similar swings. The feature vector may also include other data related to the swing event, such as for example incoming pitch trajectory or classification, outgoing ball trajectory, or game outcome (such as foul, fly-out, home run, etc.) in order to refine classification and analysis.

In situations where sensor data is unavailable or is saturated at the limit of the sensor's range for a time interval during a swing, one or more embodiments may extrapolate sensor data prior to or after the interval to estimate actual values during this interval. Extrapolation may for example use a Bézier curve. The curve may be for example a cubic Bézier curve with four control points that are selected to match the values and the slopes of the sensor data curve at the endpoints of the interval. One or more embodiments may use a Kalman filter, or a similar state space estimator, to extrapolate sensor data into the time interval. A Kalman filter may for example incorporate a kinematic model of the bat in order to predict motion parameters when sensor readings are not able to fully track the motion, for example because the motion is outside the sensor's measurement range.

BRIEF DESCRIPTION OF THE DRAWINGS

The above and other aspects, features and advantages of the ideas conveyed through this disclosure will be more apparent from the following more particular description thereof, presented in conjunction with the following drawings wherein.

DETAILED DESCRIPTION OF THE INVENTION

A baseball swing analysis method using a swing plane reference frame will now be described. In the following exemplary description numerous specific details are set forth in order to provide a more thorough understanding of the ideas described throughout this specification. It will be apparent, however, to an artisan of ordinary skill that embodiments of ideas described herein may be practiced without incorporating all aspects of the specific details described herein. In other instances, specific aspects well known to those of ordinary skill in the art have not been described in detail so as not to obscure the disclosure. Readers should note that although examples of the innovative concepts are set forth throughout this disclosure, the claims, and the full scope of any equivalents, are what define the invention.

Figure 1:
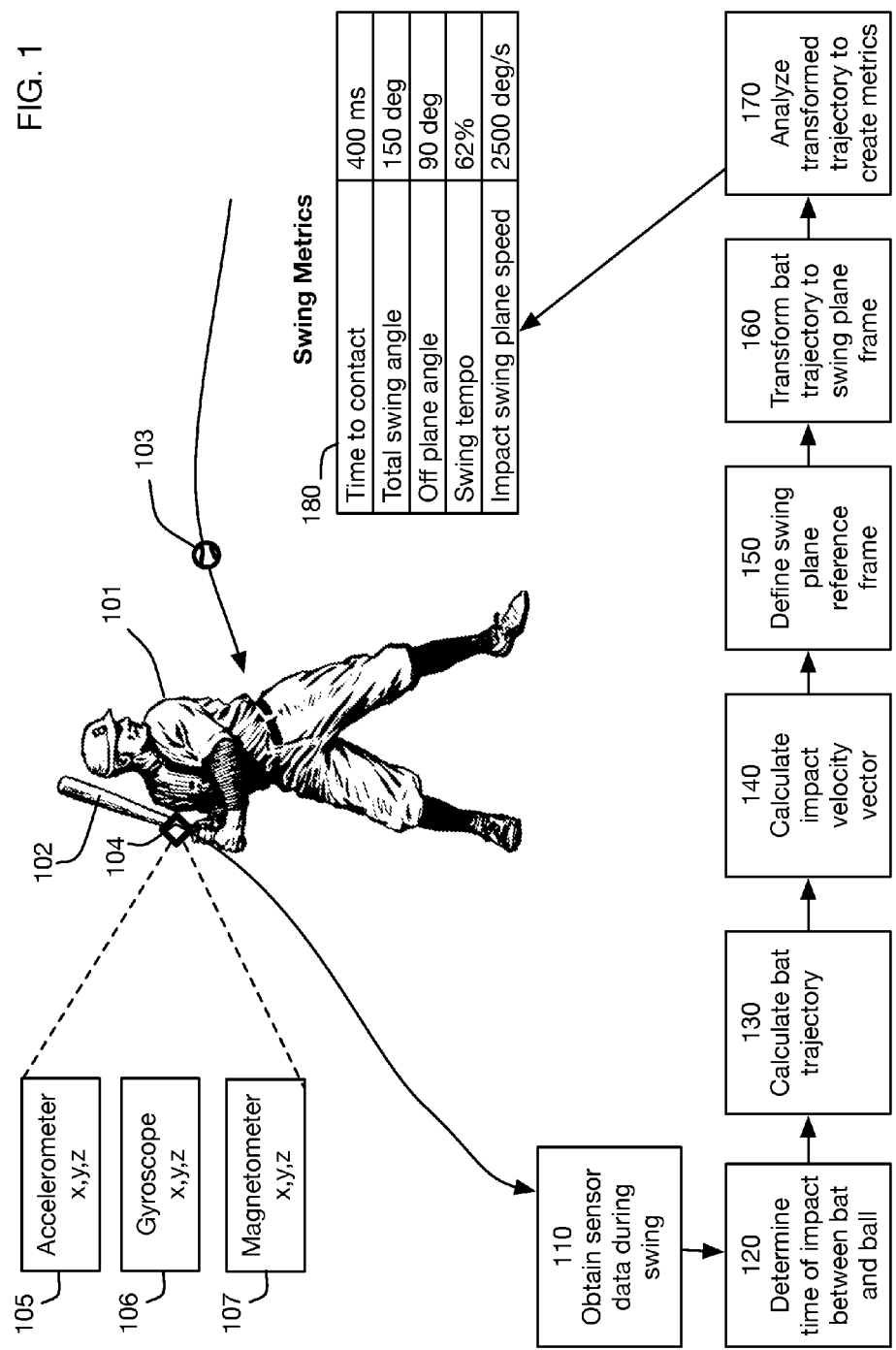
FIG. 1 shows an overview flowchart of an embodiment that processes sensor data in a swing plane reference frame to generate several swing metrics for the swing of a baseball bat.

FIG. 1 shows an overview of an embodiment of the invention. User 101 swings a baseball bat 102 to hit an incoming ball 103. Data is collected throughout the swing from sensor 104 attached to the bat. Sensor 104 may incorporate any type of sensor technology or technologies to measure any quantities, such as for example any aspects of the motion, position, or orientation of the bat. The sensor may be coupled with the proximal end of the bat, the distal end of the bat or anywhere in between. In one or more embodiments the sensor 104 may comprise two or more sensors at different locations on the bat. For example, without limitation, sensor 104 may contain any or all of a three axis accelerometer 105, a three axis gyroscope 106, and a three axis magnetometer 107. These sensor types are illustrative; one or more embodiments may use sensor data from any type or types of sensors to track the swing of bat 102. In one or more embodiments the sensor 104 may not be physically attached to the bat; for example, the sensor may be stationary and it may observe the moving bat using technologies such as video, radar, LIDAR, or ultrasound. In one or more embodiments, data from multiple types of sensors may be combined using sensor fusion. For example, sensor data from an inertial sensor on a bat may be fused with radar data or other information from external devices to calculate a bat trajectory. Sensors may measure motion or other parameters on any number of axes. Sensors may measure these parameters at any desired frequency; higher measurement frequency may for example support more detailed analysis of the swing. For example, without limitation, sensor 104 may collect data once per second, ten times per second, one hundred times per second, one thousand times per second, ten thousand times per second, or at frequencies above ten thousand times per second.

In the embodiment shown in FIG. 1, bat 102 is a baseball bat. One or more embodiments may obtain and analyze data for the swing of any type of bat or similar object, including for example, without limitation, a baseball bat, a softball bat, a cricket bat, and in one or more embodiments, a tennis racket, a table tennis racket, a badminton racket, a squash racket, a racquetball racket, a golf club, a polo mallet, a hockey stick, a field hockey stick, and a lacrosse stick.

Data from sensor 104 is obtained in step 110. One or more embodiments may use any data transfer technology or technologies to obtain sensor data. For example, without limitation, data may be transferred over a wireless network, over a wired network, or using a data storage medium that is moved from one system to another. Data may be obtained in real time during a swing, obtained after a swing occurs, or obtained using a combination of real-time transfer and transfer after a swing event.

Steps 120 through 170 analyze data from sensor 104 to characterize the swing, resulting in swing metrics 180. These steps may be performed in any order, or in parallel. These steps may be performed on any system or combination of systems. For example, without limitation, any or all of these steps may be performed on a computer, a mobile computer, a laptop computer, a notebook computer a desktop computer, a tablet computer, a mobile phone, a smart phone, a smart watch, a microprocessor, a server, or a network of any of these devices. In one or more embodiments the sensor 104 may contain a processor or processors that perform some or all of the steps 110 through 170.

Step 120 determines the time of impact between bat 102 and ball 103. This step may for example detect a signature in the sensor data that indicates a collision. For example, if sensor 104 includes an accelerometer such as accelerometer 105, a rapid spike in acceleration may be a signature of an impact. Similarly, if sensor 104 includes a gyroscope such as gyroscope 106, a rapid reduction in angular velocity may be a signature of an impact. One or more embodiments may for example use sensors that directly measure impact, such as pressure sensors or contact switches. In one or more embodiments, a swing endpoint may be defined even if the bat does not hit the ball, for example during practice swings, air swings, or strikes. This swing endpoint may be based for example, without limitation, on parameters such as the location of the bat relative to the plate or to an incoming ball, the aim angle of the bat, or the point in time when the bat achieves maximum velocity or maximum angular velocity. A calculated swing endpoint may be used instead of an actual impact time for any of the subsequent metric calculations described below.

Step 130 calculates a trajectory of the bat 102 from a starting point of the swing through the impact time determined in step 120. In one or more embodiments the trajectory may also extend beyond the impact or prior to the start of the swing. The bat trajectory may be a time series of motion data samples, each of which represents the state of the bat at a point in time during the swing. For example, each sample may include data on any or all of the bat's position, orientation, velocity, angular velocity, acceleration, or angular acceleration. In one or more embodiments a sample may include data for multiple locations on the bat. Methods to calculate an object's trajectory from motion sensor data are known in the art. For example, one or more embodiments may use inertial navigation algorithms known in the art to calculate the position and orientation of the bat over time from acceleration data (for example from accelerometer 105) and from angular velocity data (for example from gyroscope 106). Data from other sensors, such as for example magnetometer 107, may for example provide redundant measurements to correct errors in inertial navigation algorithms.

Because the orientation and position of sensor 104 changes throughout the swing, the bat trajectory calculated in step 130 may not be in a convenient form for analysis. Therefore, in step 150 a standardized reference frame is defined based on the swing itself. We refer to this reference frame as the swing plane reference frame. In step 160 the bat trajectory is transformed to this reference frame. In step 170 the transformed trajectory is used to analyze the swing, and to generate one or more swing metrics describing and characterizing the swing. Illustrative swing metrics 180 describe for example the timing of the swing, the speed of the swing, and the angles traversed during the swing.

Figure 2:
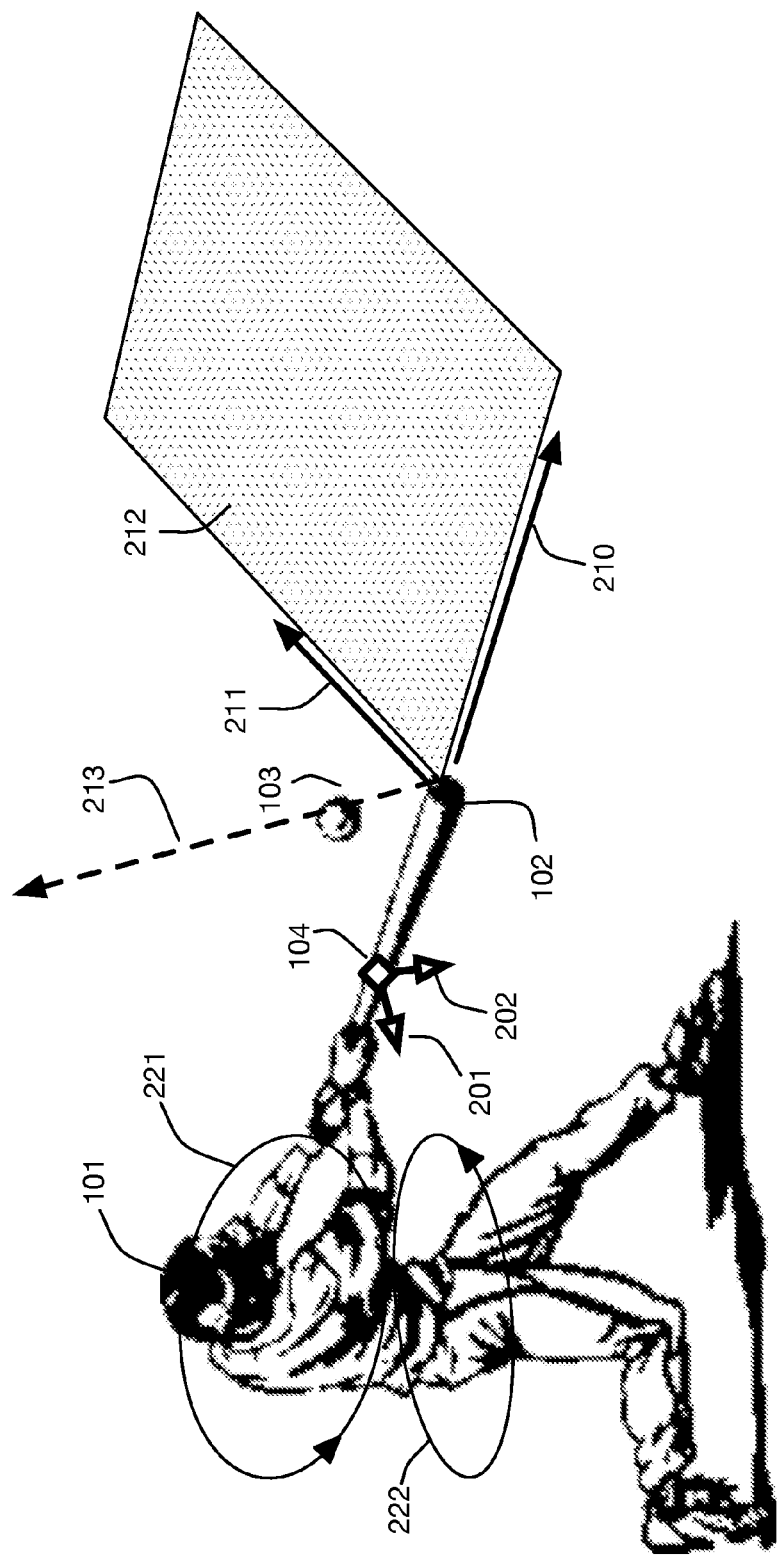
FIG. 2 shows a reference frame based on a swing plane defined by the bat orientation and by the velocity vector of the bat at the time of impact with the ball.

FIG. 2 illustrates definition and calculating of the swing plane reference frame. This reference frame is defined by the bat's orientation and motion at the time of impact between the bat 102 and the ball 103. A swing plane 212 is defined by two axes: a first axis 210 is the longitudinal axis of the bat (along the bat's long dimension); a second axis 211 is in the direction of the bat's velocity at the time of impact. The velocity vector at impact may also be calculated as a tangent vector to the bat's instantaneous rotation round the angular velocity axis. This impact velocity vector 211 may be calculated or obtained from the bat trajectory. In one or more embodiments a specific point on the bat, such as for example the sweet spot, may be used to define the impact velocity vector. The swing plane 212 is the plane spanned by the vectors 210 and 211. To complete the reference frame, a third orthogonal off-plane axis 213 is selected as the normal vector to the plane 212. The swing plane 212 defined by the axes 210 and 211 provides a reference frame that can be calculated from data generated by bat sensor 104. Other planes of rotation that may be relevant to the kinematics of the swing include for example the rotational plane 221 for the batter's shoulders, and the rotational plane 222 for the batter's hips. In one or more embodiments additional sensors, for example sensors attached to the batter's shoulders and hips, may be used to calculate these body rotational planes in addition to the swing plane 212.

Figure 3:
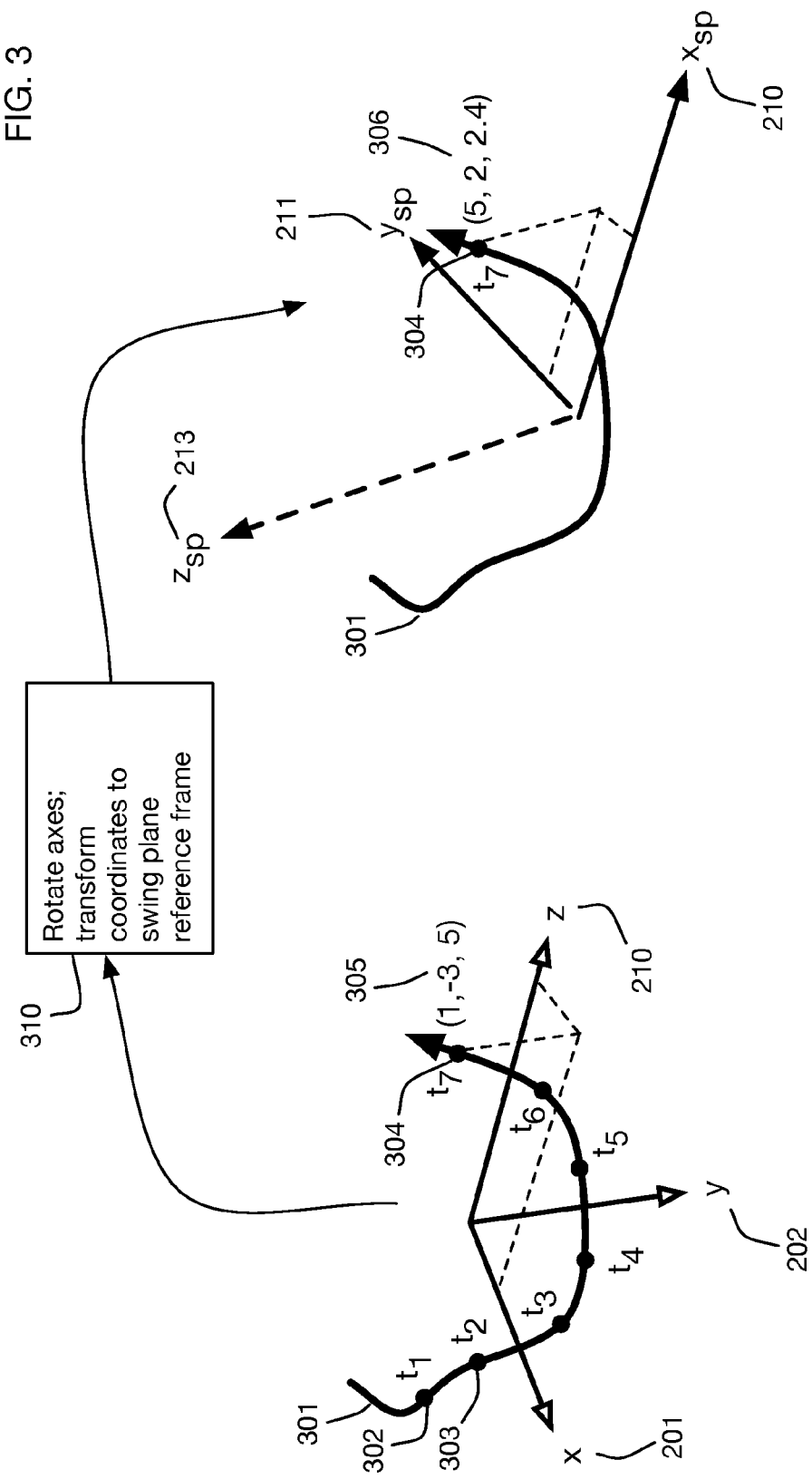
FIG. 3 illustrates transformation of a bat trajectory from a local sensor frame to the swing plane reference frame of FIG. 2.

In the example shown in FIG. 2, sensor 104 has a local reference frame in which sensor data is measured. This local reference frame in general may have a completely different orientation from the swing plane reference frame defined by axes 210, 211, and 213. For example, the sensor local reference frame may have axes 201, 202, and 210; in this example one axis of the sensor local reference frame is aligned with the bat longitudinal axis, but the other axes are in arbitrary directions due to the rotational symmetry of the bat around this axis. To facilitate standardized analysis of swings and comparison of swings across players, bat trajectory information is transformed from the sensor local reference frame into the swing plane reference frame. FIG. 3 illustrates this transformation. Bat trajectory 301 includes motion data samples at various points in time, such as for example points 302, 303, and 304. These samples may include any information on the state of the bat, such as position, orientation, or derivatives of these values like velocity and angular velocity. For illustration, the bat trajectory 301 is shown as a single curve in three dimensional space (for example as a curve of bat position over time); however, in one or more embodiments the bat trajectory may include any data with any number of dimensions. In the sensor local reference frame defined, for illustration, by axes 201, 202, and 210, each sample point has coordinates such as coordinates 305 for point 304. Transformation 310 maps the sample points into the swing plane reference frame, for example using a rotation of the axes 201, 202, and 210 into axes 210, 211, and 213. For example, in the swing plane reference frame, point 304 on the bat trajectory 301 has coordinates 306.

Figure 4:
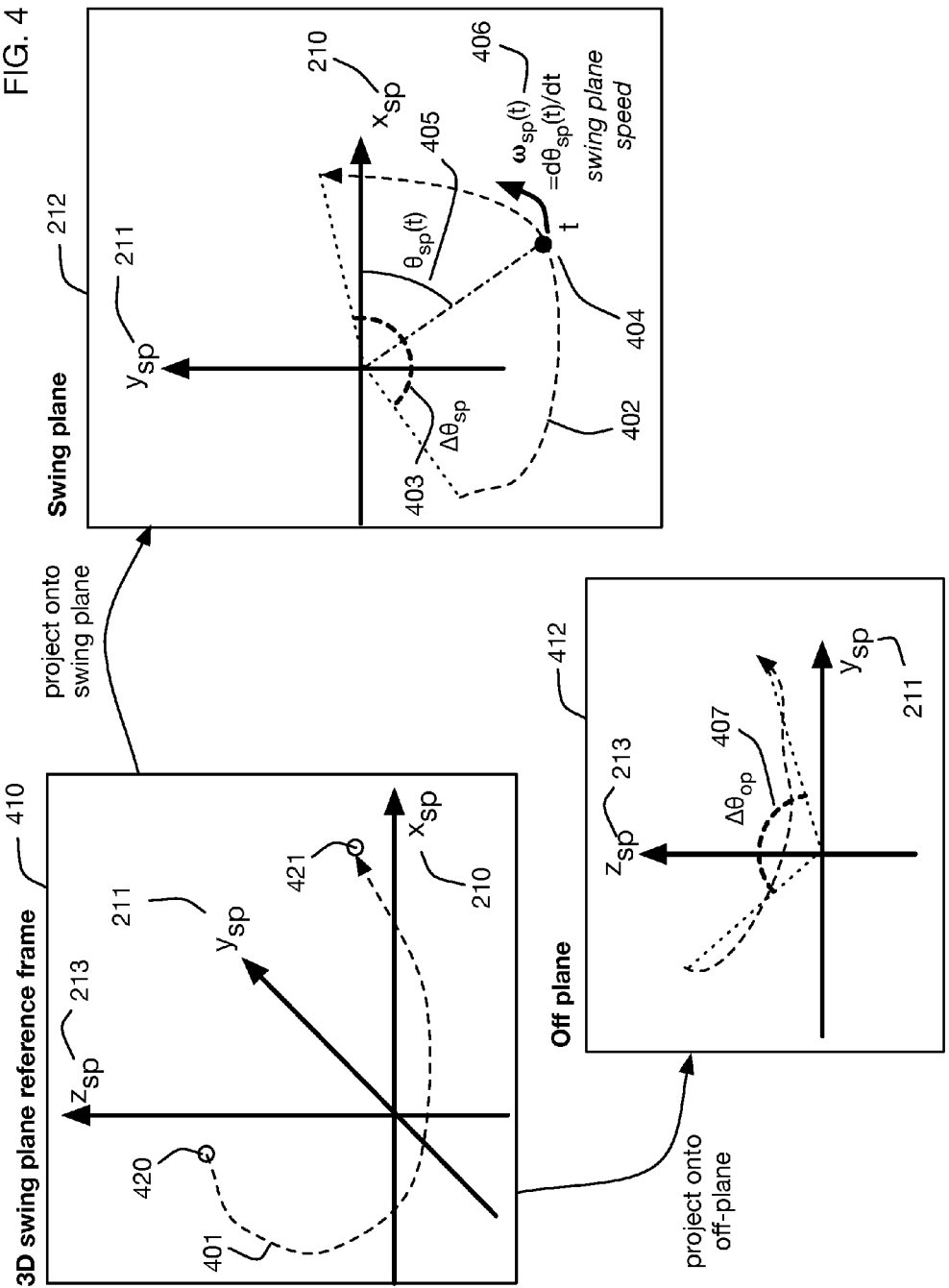
FIG. 4 illustrates various metrics derived from the swing plane reference frame, including a total swing angle in the swing plane, an off-plane swing angle, and a swing plane speed.

One or more embodiments of the invention may analyze the bat trajectory in the swing plane reference frame to measure and characterize the swing. FIG. 4 shows illustrative metrics for angular change that are defined relative to the swing plane reference frame. Bat trajectory 401 is a three dimensional curve in the three dimensional swing plane reference frame 410 defined by axes 210, 211, and 213. Trajectory 401 has starting point 420, representing a start of the swing, and endpoint 421, representing for example the time of impact between the bat and the ball. This curve may be projected onto the two-dimensional swing plane 212 defined by axes 210 and 211, and various metrics may be calculated from this projection. For example, the 2D curve 402 is the projection of the bat trajectory 401 onto plane 212. As the curve 402 proceeds from the starting point to the endpoint of the trajectory, it subtends an angle 403 ($\Delta\theta_{sp}$) in the swing plane (with vertex at the origin). This angle 403, which we refer to as the total swing angle, is a swing metric that indicates the total amount of bat movement during the swing in the swing plane. Similarly, the bat trajectory 401 may be projected onto a plane 412 orthogonal to the swing plane, and the angle 407 subtended by the projected trajectory is a different swing metric that we refer to as the off-plane angle. The total swing angle metric and the off-plane angle metric provide a useful characterization of how the batter is moving the bat through the swing. Projection of the trajectory 401 onto swing plane 212 also provides a measure of the instantaneous angular velocity 406 of the trajectory at any point in time, such as at illustrative point 404. This instantaneous angular velocity in the swing plane, which we refer to as the swing plane speed, is a more useful metric of the bat's motion than for example the total linear velocity of the bat, which includes an off-plane component of velocity that is not as relevant for the power of the swing. The swing plane speed 406 may be calculated for example as the derivative of the instantaneous angle 405 between the point 404 on the projected trajectory 402 and the axis 210. In one or more embodiments that include a gyroscope, which measures angular velocity directly, the swing plane speed may be calculated by projecting the measured angular velocity onto the axis orthogonal to the swing plane 212.

Figure 5:
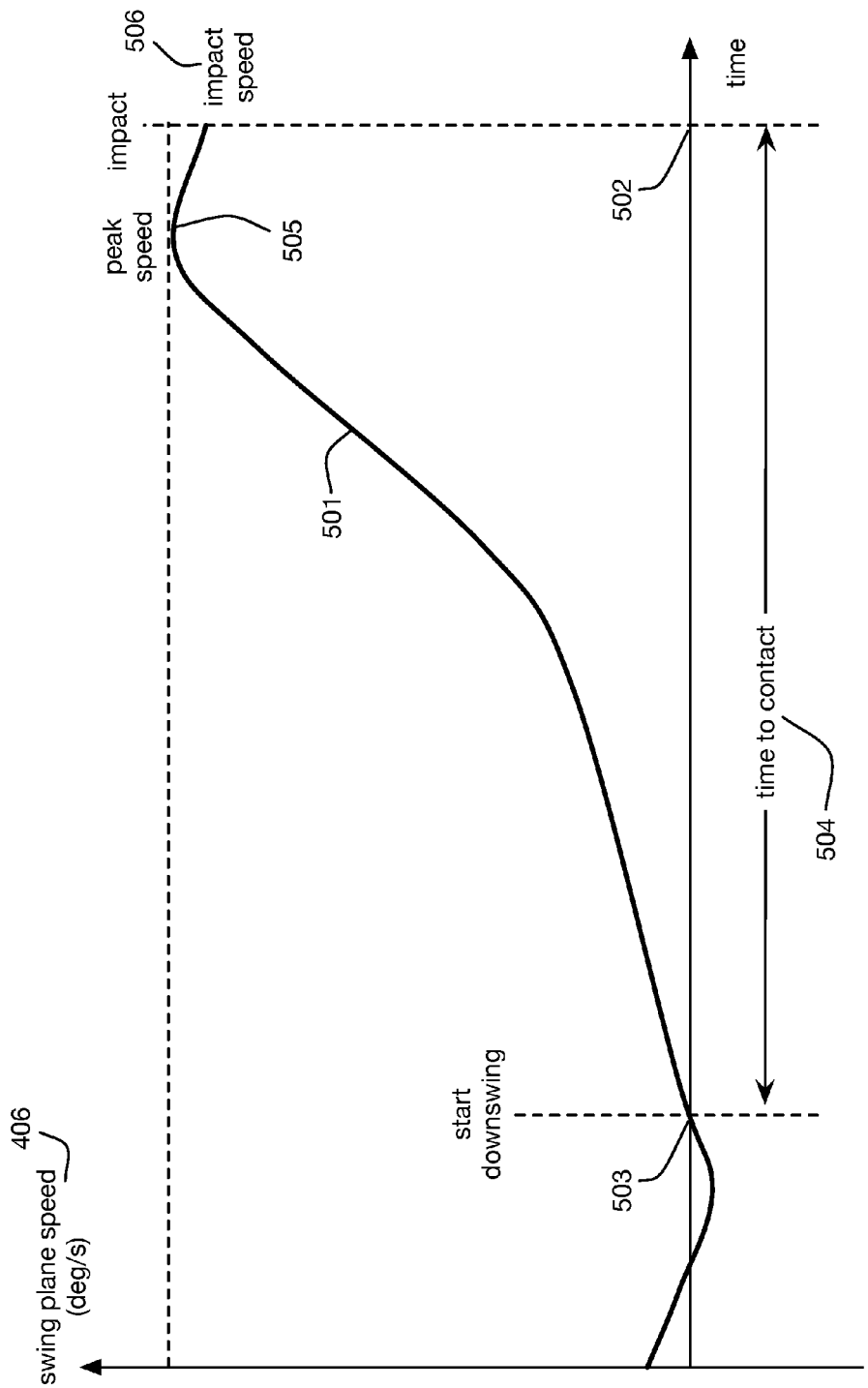
FIG. 5 illustrates derivation of a time to contact swing metric that measures how quickly the batter responds.

The curve of swing plane speed over time through the swing provides additional useful information about the swing. FIG. 5 shows an illustrative curve 501 of the swing plane speed 406 as a function of time. The curve typically increases through the swing as the batter accelerates the bat. The swing plane speed reaches a maximum value 505 during the swing. For some swings, the peak speed 505 may occur at the time of impact 502; however, this is not necessarily the case for all swings. The impact swing plane speed 506 is an important swing metric since it greatly affects the distance and power of the hit. The swing plane speed curve may be used to define an unambiguous point in time for the start of the downswing of a swing: this start of downswing 503 may be defined as the last point in time when the swing plane speed is zero prior to the impact. This definition is based on an unambiguous physical event rather than an arbitrarily defined threshold crossing. This provides a clear advantage in terms of metric consistency and physical significance. If there is no zero crossing, as is the case in certain swing styles, we define the start of downswing where the slope and magnitude of the swing plane component meet certain threshold criteria. This fallback definition does not provide the clear advantages of the zero crossing; however, because it is based on the swing plane component, it provides greater consistency than a definition based on vector magnitude, particularly across heterogeneous swing styles where much of the variability (e.g., bat waggle) occurs in the off-plane component.

Using the start of downswing 503 and the time of impact 502, a total swing time, which we refer to as the time to contact metric, may be defined as the difference 504 between the impact time 502 and the start of downswing time 503. This time to contact metric is an important metric related to the batter's ability to read the pitch.

Figure 6:
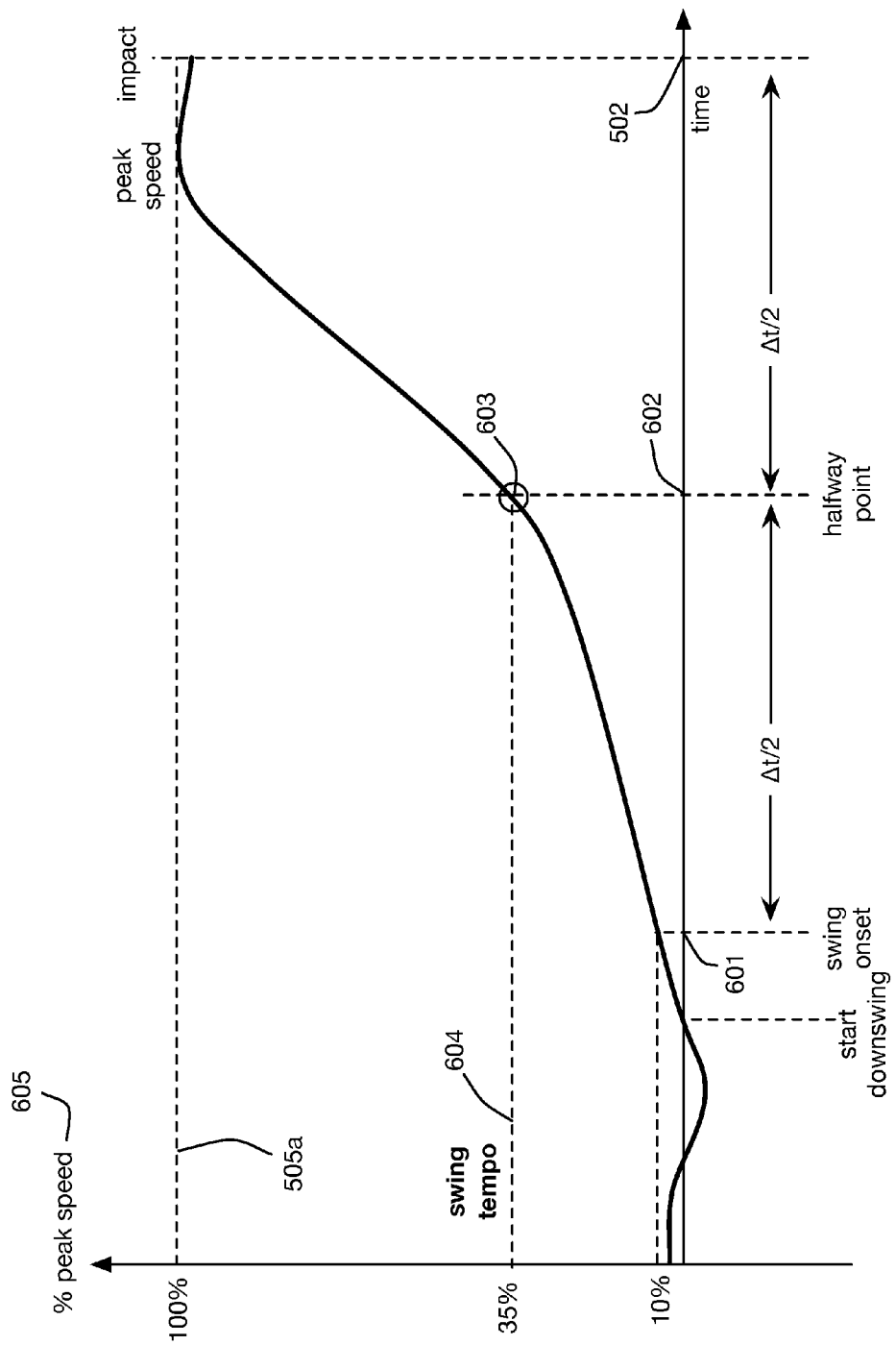
FIG. 6 illustrates derivation of a swing tempo metric based on swing plane speed, which indicates how quickly the swing plane speed increases through the swing.

The rate at which the swing plane speed increases through the swing also provides a useful metric. FIG. 6 illustrates a method to standardize this metric by measuring the fraction of the peak speed achieved at the halfway point of the swing. To allow meaningful comparison across players with different swing styles, the swing plane speed curve is normalized so that swing plane speed is measured as a percentage 605 of the peak speed. Thus the normalized swing speed curve starts at zero at the start of downswing, and increases to 100% at the peak speed. A halfway point 602 is defined for the swing, and the fraction 603 of the peak speed at this point is defined as the swing tempo metric 604. In one or more embodiments the halfway point may be defined as halfway between the start of downswing and the time of impact. However, empirical analysis of swings shows that a more robust halfway point may be defined by selecting a swing onset time 601 as a time at which the swing plane speed reaches a specified small fraction of the peak speed, such as for example 10%, and by defining the halfway point as halfway between the swing onset time and the time of impact.

This definition of the swing tempo metric is based on the insight from comparing statistical distributions, where the greatest variability in deviation from an ideal curve occurs at the half-way point between two fixed endpoints. The significance of this metric comes from an understanding of the kinematic chain (hips, shoulders, arms, wrists) for transferring energy from the body to a baseball bat. A rotationally efficient swing will derive a certain amount of energy from the hips and shoulders compared to the arms and wrists. We can infer how rotationally efficient a baseball swing is by the percentage of speed in the "body" half of the swing relative to the "arm" half. An ideal swing tempo range is learned from empirical data collected from elite-level batters. Deviation from the ideal tempo range, either high or low, is used to provide feedback and prescribe drills to the batter in order to improve performance. A low tempo typically indicates that the swing is dominated by arms (e.g., casting), while a high tempo indicates that a swing is dominated by body (at the expense of bat control).

In one or more embodiments, additional tempo metrics may be defined at other points in a swing, in addition to the halfway point tempo metric described above. For example, without limitation, an early tempo metric may be defined as the fraction of peak speed achieved at the 25% point of the swing, a mid-tempo metric may be defined as the fraction of peak speed achieved at the 50% point of the swing (as discussed above), and a late tempo metric may be defined as the fraction of peak speed achieved at the 75% point of the swing. The three tempo metrics may isolate the effect of different segments of the kinematic chain of the swing; for example, the early tempo metric may characterize the rotation of hips and torso, the mid-tempo metric may characterize the rotation of the torso and arms, and the late tempo metric may characterize the rotation of the arms and bat. These percentages are illustrative; one or more embodiments may measure swing tempo at any point or points in a swing.

Figure 7:
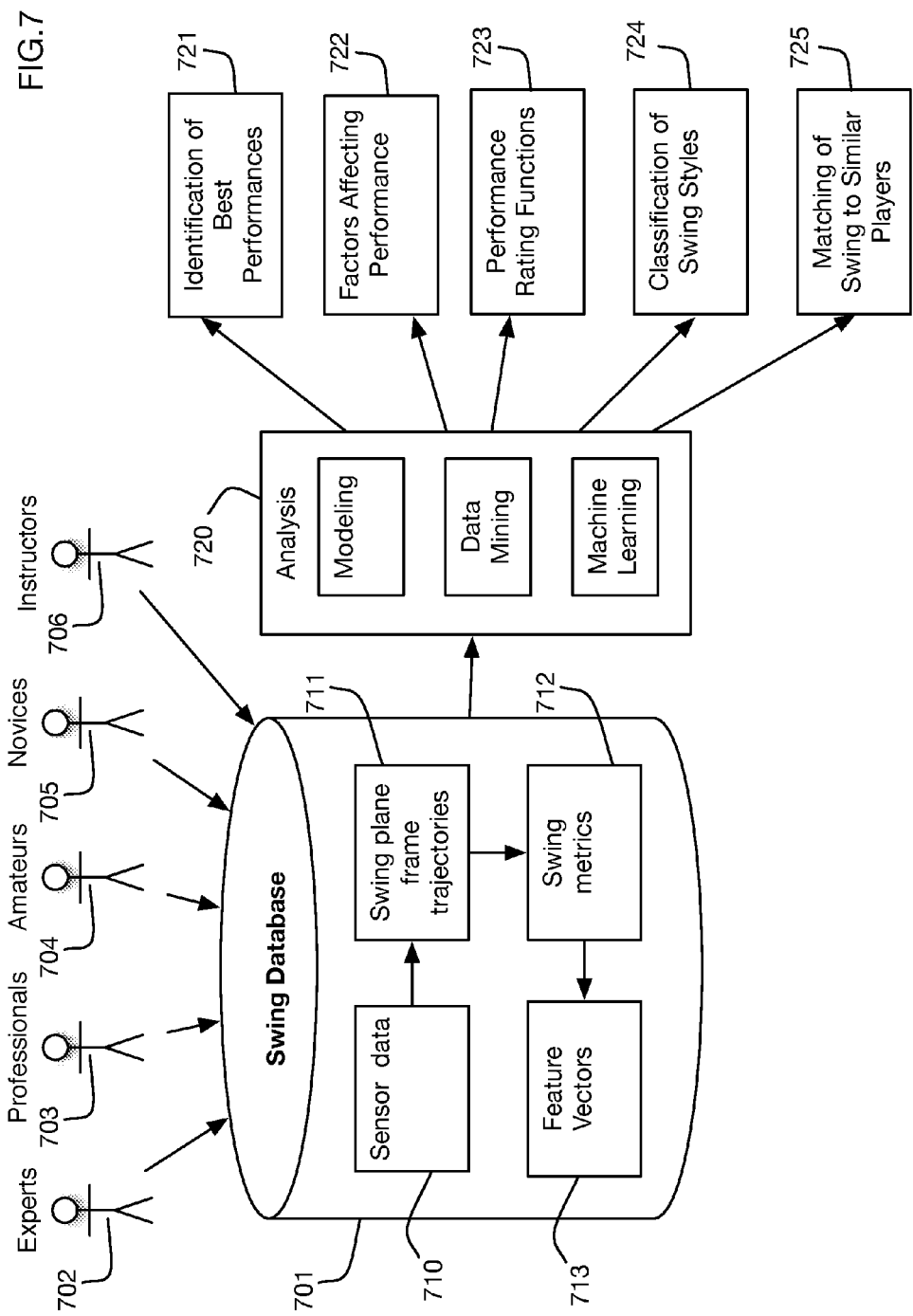
FIG. 7 illustrates an embodiment that collects swing data from multiple users into a swing database, and that analyzes this database to generate methods of rating and classifying swings.

In one or more embodiments, swing data and swing metrics may be collected from multiple users and organized in a swing database for further analysis. FIG. 7 illustrates an embodiment that collects data into swing database 701 from multiple types of users, including for example, without limitation, experts 702, professionals 703, amateurs 704, novices 705, and instructors 706. Data in the swing database may include for example, without limitation, sensor data 710, bat trajectories in the swing plane frame 711, and swing metrics 712 (such as for example the total swing angle, off-plane angle, time to contact, impact swing plane speed, and tempo metrics described above). Multiple metrics may be combined into feature vectors 713 that may be used to classify, categorize, compare, or analyze swings. Data from the database may be used for various analysis procedures 720, which may include for example any or all of modeling swings and batters, data mining the database for patterns or trends, and applying machine learning techniques to learn relationships, functions, or categories. Outputs of the analyses 720 may include for example identification of best performances 721 that flag certain swings or groups of swings as illustrative of ideal or maximum performance; factors affecting performance 722 that identify swing characteristics that contribute to or detract from high performance; performance rating functions 723 that rate swings on how close they are to ideal performance levels; classifications of swing styles 724 that map swings into categories reflecting similar characteristics or similar performance; and matching of swings to similar players 725 that indicate which other swings or other players are most similar to a given swing or player.

Figure 8:
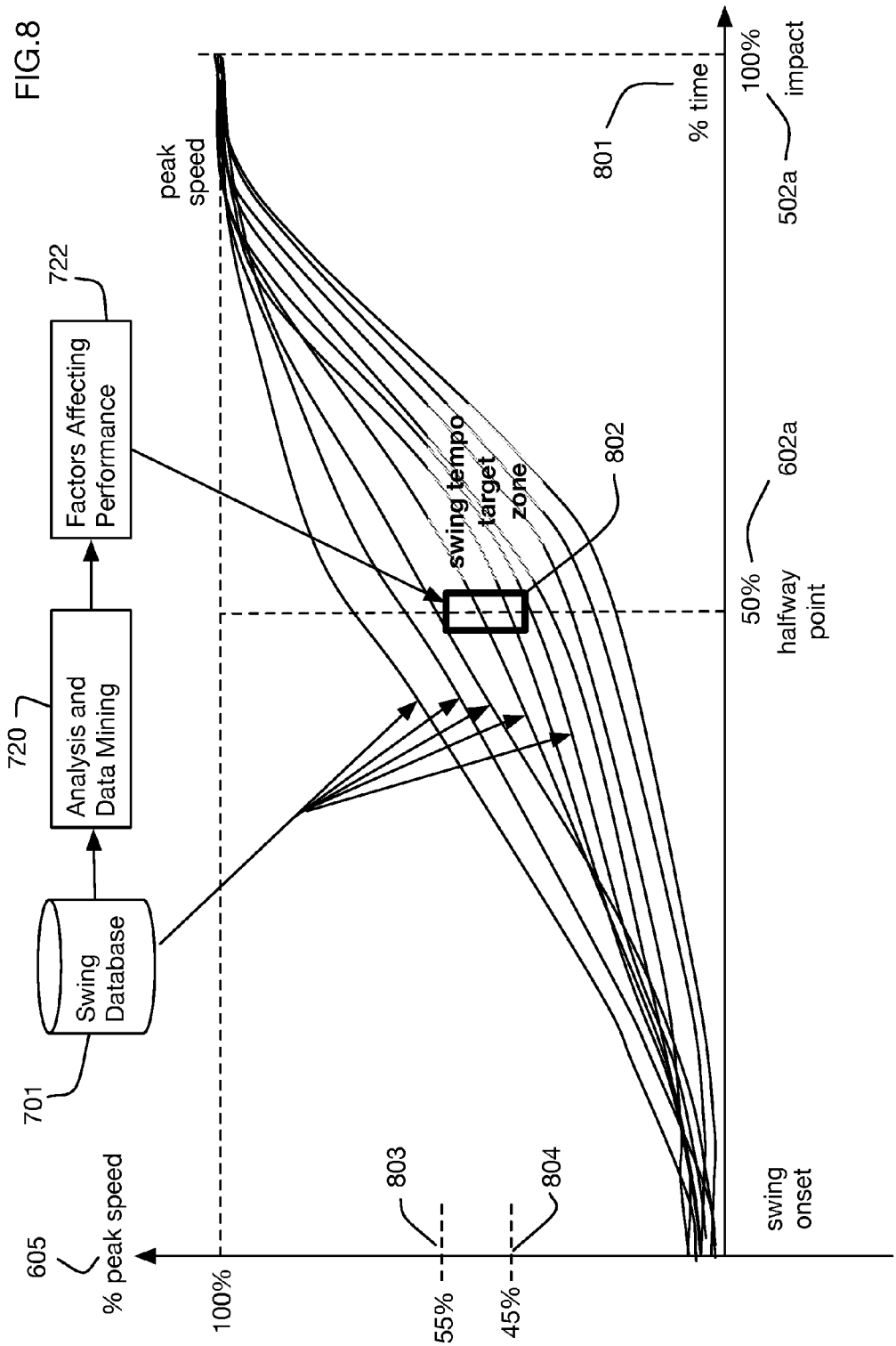
FIG. 8 illustrates an embodiment that analyzes swing tempo from multiple users to determine a target zone for peak performance.

FIG. 8 illustrates an example of the data analysis methods described with respect to FIG. 7, using the swing tempo metric defined above. Using swing database 701 as input, data analysis and data mining process 720 compares swing plane speed curves across players to determine factors affecting performance 722. This analysis indicates that best performance occurs when swing tempo is in a target zone 802, for example in a range between 804 and 803. This analysis uses normalized swing plane speed curves for the swings in database 701, with the swing plane speed axis normalized to the percentage of peak speed 605, and the time axis 801 normalized to a percentage of swing time between swing onset (0%) and impact 502a (100%). The normalized swing plane speed at halfway point 602a (50%) is the swing tempo metric for each swing.

Figure 9:
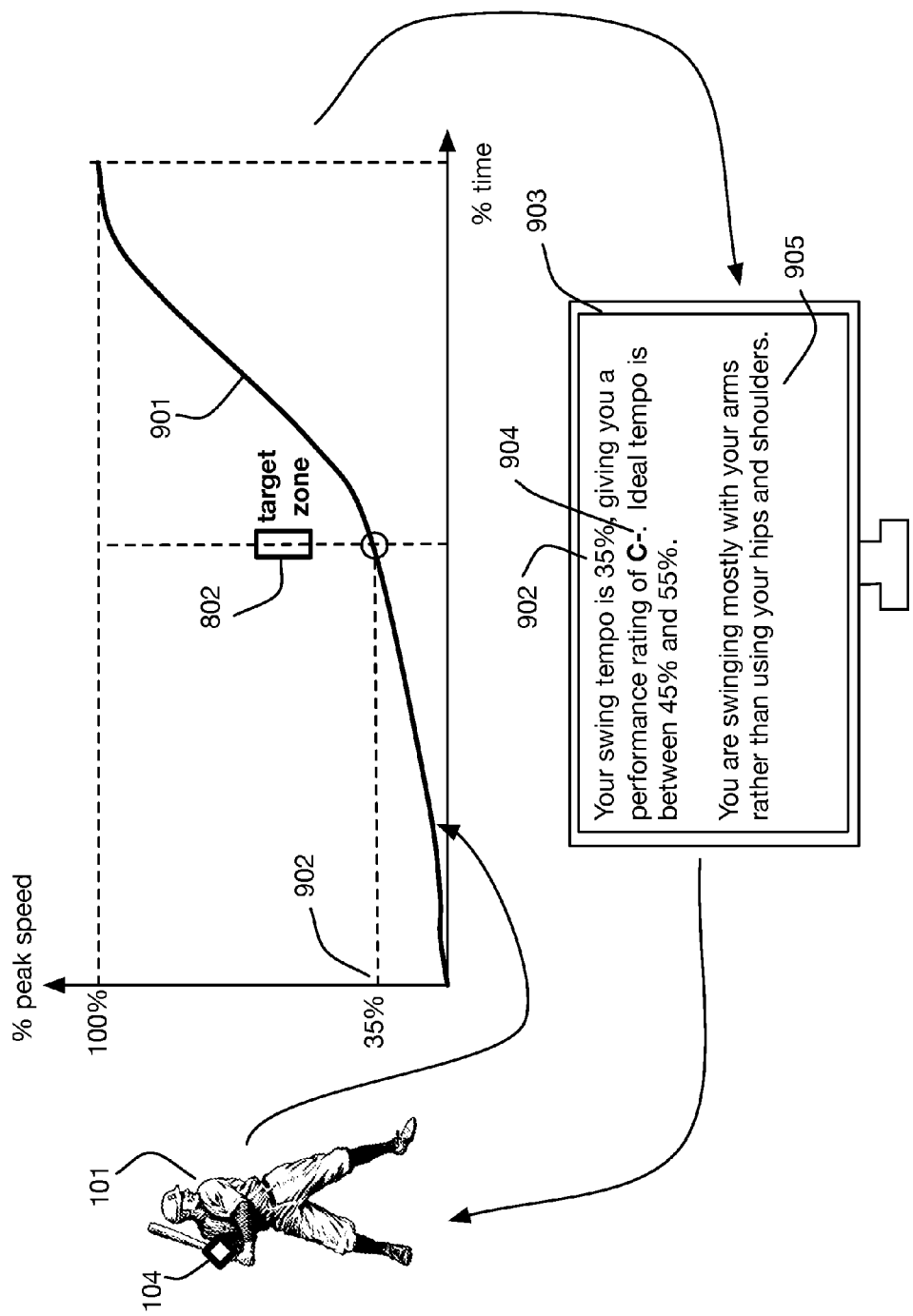
FIG. 9 shows an embodiment that provides feedback to a user on his or her swing by comparing the swing tempo to the target zone described in FIG. 8.

Using the analysis illustrated in FIG. 8, an individual swing may be evaluated by comparing it to the empirically derived criteria for best performance. FIG. 9 illustrates an example with batter 101 generating a swing plane speed curve 901 for a swing. The measured swing tempo 902 for this swing is compared to the target zone 802 in order to rate the swing's performance. Feedback is then provided to batter 101, for example on computer screen 903. This feedback provides the swing tempo metric 902, as well as a performance rating 904 that is based on comparing the swing to performance criteria derived from empirical analysis. The feedback may also include specific critiques such as 905 that diagnose the swing or suggest corrections or improvements.

One or more embodiments may provide feedback to a batter or to other users (such as a coach or trainer) using any desired method or system. For example, without limitation, feedback may be displayed on any computer, laptop, notebook, tablet, mobile phone, smart watch, or wearable device. Feedback may be provided using a specific app, or transmitted via general messaging systems such as email or text messages. Feedback may be audio, visual, haptic, or any combination thereof.

Figure 10:
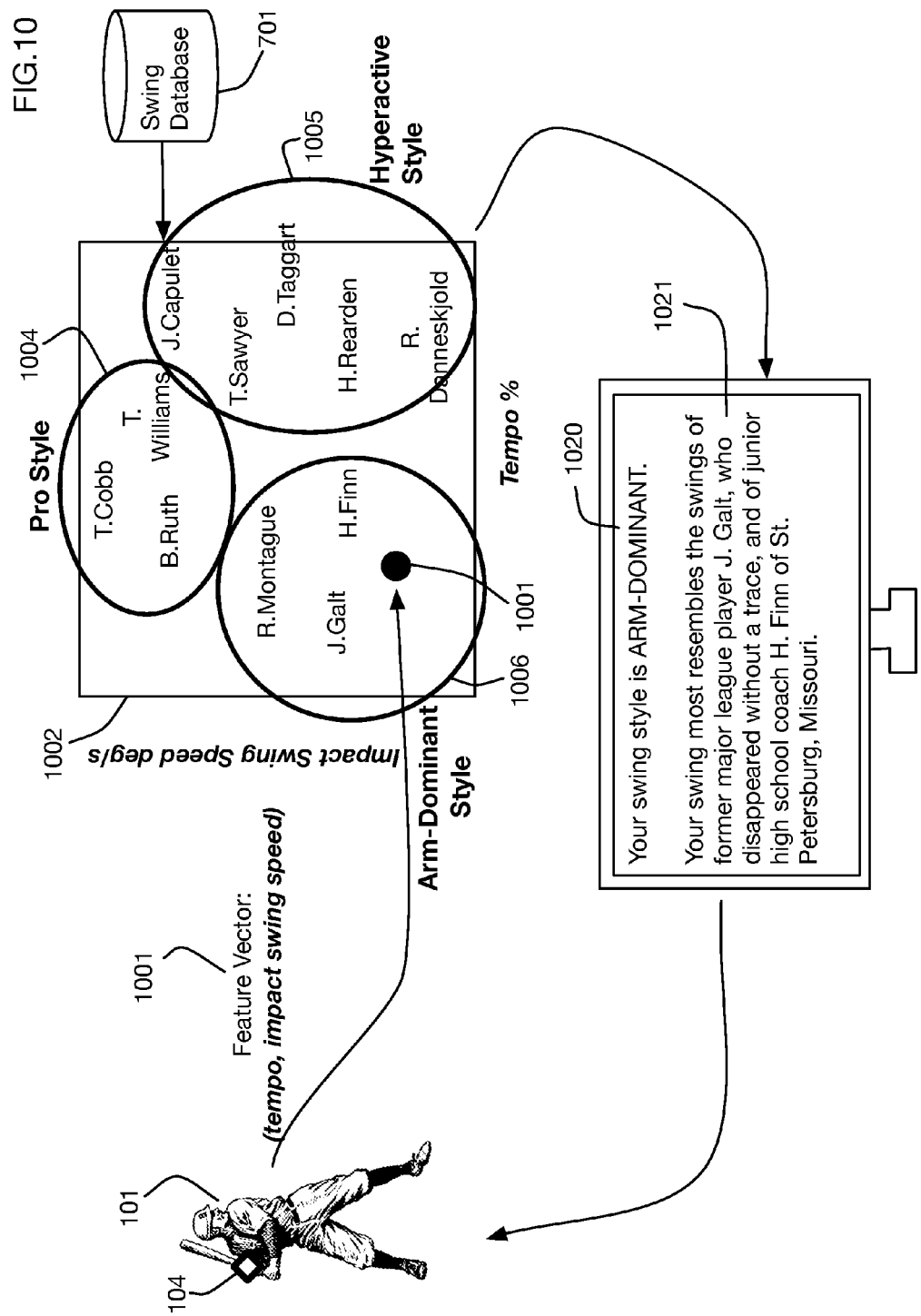
FIG. 10 illustrates an embodiment that classifies swings into swing styles based on a feature vector that combines multiple swing metrics; feedback to a user indicates the swing style as well as identifying other players with similar swings.

FIG. 10 continues the example of FIG. 9 to illustrate additional analysis and feedback for a swing based on comparisons with swings in a swing database. In this example, a feature vector 1001 is generated for a particular swing by batter 101. For illustration, this feature vector is a combination of the swing tempo and the impact swing plane speed. One or more embodiments may generate feature vectors using any combinations of metrics or of any data derived from sensor data or bat trajectories. Swings from swing database 701 are compared on grid 1002 using this feature vector, and are analyzed (for example using cluster analysis techniques known in the art) to categorize swings into a set of swing styles. For example, the analysis may partition swings into three swing styles 1004, 1005, and 1006. The feature vector 1001 corresponding to the swing by batter 101 places the swing into swing style cluster 1006. Feedback to the batter indicates this swing style 1020. In addition, the batter's swing may be matched against typical swings from other users to provide feedback 1021 that identifies other users with swings that resemble the batter's swing.

Figure 11:
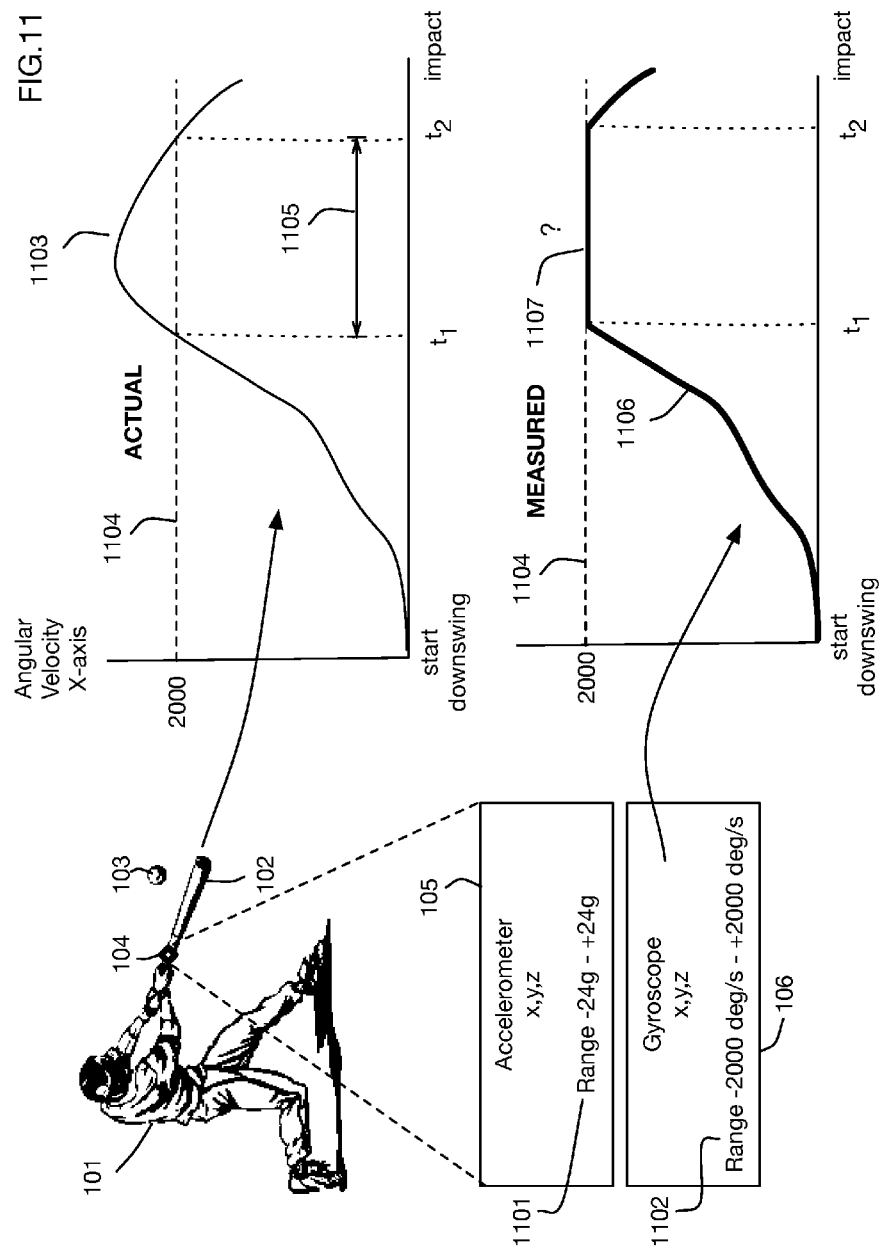
FIG. 11 shows a potential issue that may arise when a sensor has a limited range and the actual motion of the bat exceeds this measurement range during a time interval within the swing.

In some situations, one or more of the sensors that measure the motion the bat may have insufficient range to measure the complete motion throughout the entire swing. FIG. 11 shows an example of this situation where the sensor 104 on bat 102 includes accelerometer 105 with range 1101, and gyroscope 106 with range 106. Taking the angular velocity around the x-axis of the sensor as an illustrative example, the actual x-axis angular velocity 1103 exceeds the upper limit 1104 of measurement range 1102 during time interval 1105. Therefore, the measured sensor values 1106 cannot track the true values 1103 of the motion during this interval 1105. Instead the measured value 1107 during this interval is saturated at the upper limit 1104. This saturation may affect the accuracy of swing metrics. This example using the x-axis of the gyroscope is illustrative; a similar issue may occur with any sensor (including for example the accelerometer 105 as well as the gyroscope 106) and with data from any axis of any sensor.

Figure 12:
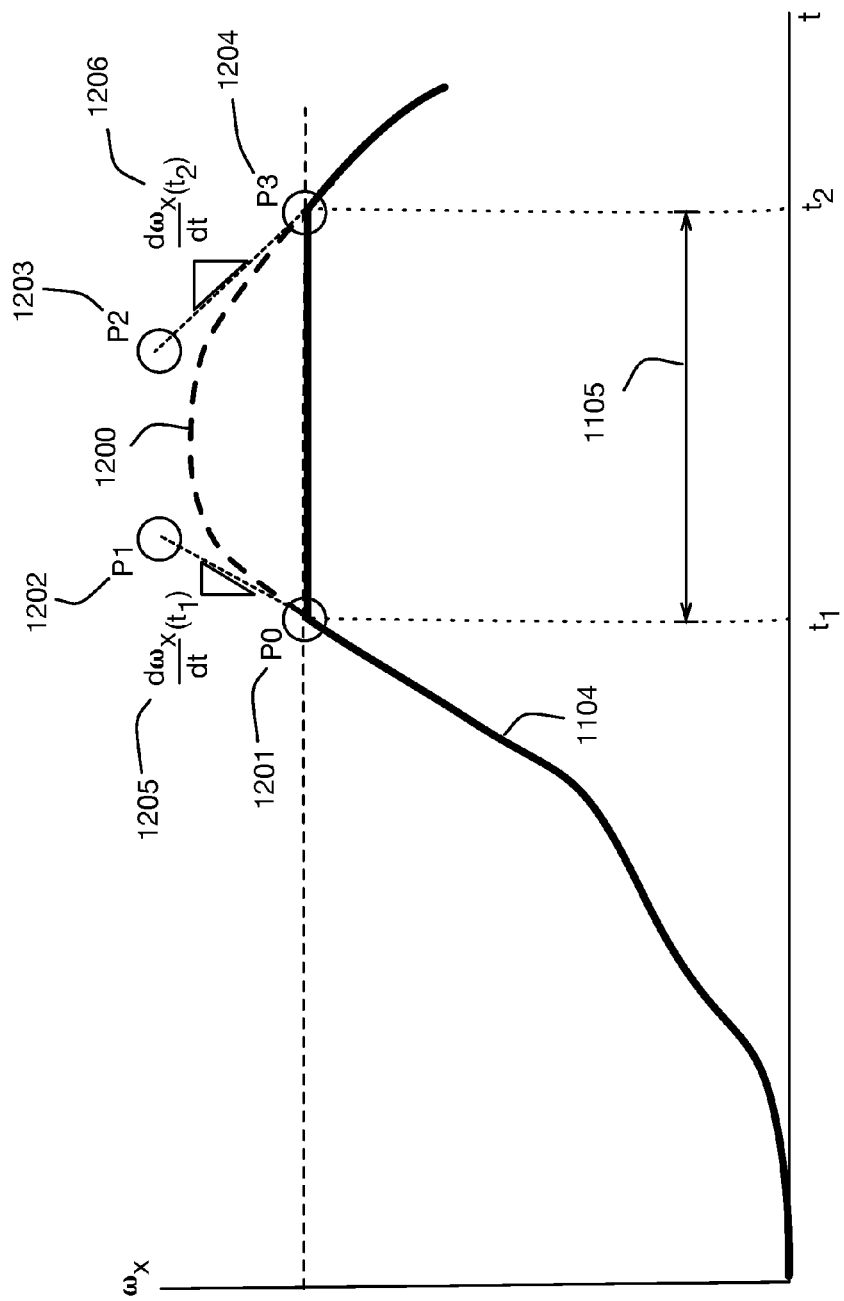
FIG. 12 illustrates an embodiment that addresses the limited range situation shown in FIG. 11 by extrapolating sensor data from before and after the time interval, in this example using a cubic Bézier curve.

To address this issue, one or more embodiments of the invention may extrapolate sensor data from prior to or after the time interval 1105 when the sensor is saturated. Extrapolation may also be used when sensor data is unavailable for a period of time for any other reason, for example because of a limited sampling rate, a recalibration period, or a defective sensor. Extrapolation may be used for any sensor or sensors, or any axis of any sensor or sensors. Embodiments may use any method to extrapolate sensor data into any time interval. FIG. 12 illustrates an embodiment that extrapolates sensor data from both endpoints of the time interval by constructing a Bézier curve 1200 for the values in the interval. In this example, the curve 1200 is a cubic Bézier curve defined by the four control points 1201, 1202, 1203, and 1204. This is illustrative; one or more embodiments may use Bézier curves or any other splines or curves of any order. Control points 1201 and 1204 match the values of the sensor measurements 1104 at the endpoints of interval 1105. The internal control points 1202 and 1203 are chosen to match the slopes of curve 1104 at these endpoints. Specifically, the tangent value 1205 of the curve 1104 at point 1201 is the slope of the line between control points 1201 and 1202, and the tangent value 1206 of the curve 1104 at point 1204 is the slope of the line between control points 1203 and 1204. Points 1202 and 1203 may also be chosen to limit for example the maximum value of the curve 1200 in the interval.

One or more embodiments may select control points for a Bézier curve in such a way as to satisfy the initial and/or final conditions (magnitude and slope) and also to satisfy additional constraints on the maximum absolute value and maximum extrapolation duration. For two-sided extrapolation (no impact events), four control points may be used as shown for example in FIG. 12: the initial and final points are placed where the curve crosses the saturation threshold, and two interior control points are along a line matching the slope of the curve at some distance, which is constrained by some maximum time duration and by a maximum absolute value. This approach provides control of the shape of the extrapolation curve better than a cubic polynomial fit, which will match the same slope and value constraints but may exceed the other physical constraints. If the initial or final edge of the saturation interval is an impact event, then the unconstrained edge may be represented by a single control point, resulting in a three-point Bézier curve. Again, the time and value for this single control point may be selected to achieve the desired shape of the extrapolated curve into the impact event. Because a Bézier curve is not parametric in time, it may be necessary to resample the extrapolated curve at the original sample times. This type of Bézier extrapolation may be applied to an individual saturated sensor axis (independent of the other components) or a composite value (e.g., the x-y resultant or total vector magnitude). The shape of the composite curve may be easier to model or constrain than the underlying individual components for particular kinematic events, resulting in increased accuracy of the extrapolated result. If the underlying component values are needed, they can be obtained by solving for the unknown saturated component(s) from the extrapolated composite result and unsaturated component values (the result will be under-determined if more than one component is saturated).

Figure 13:
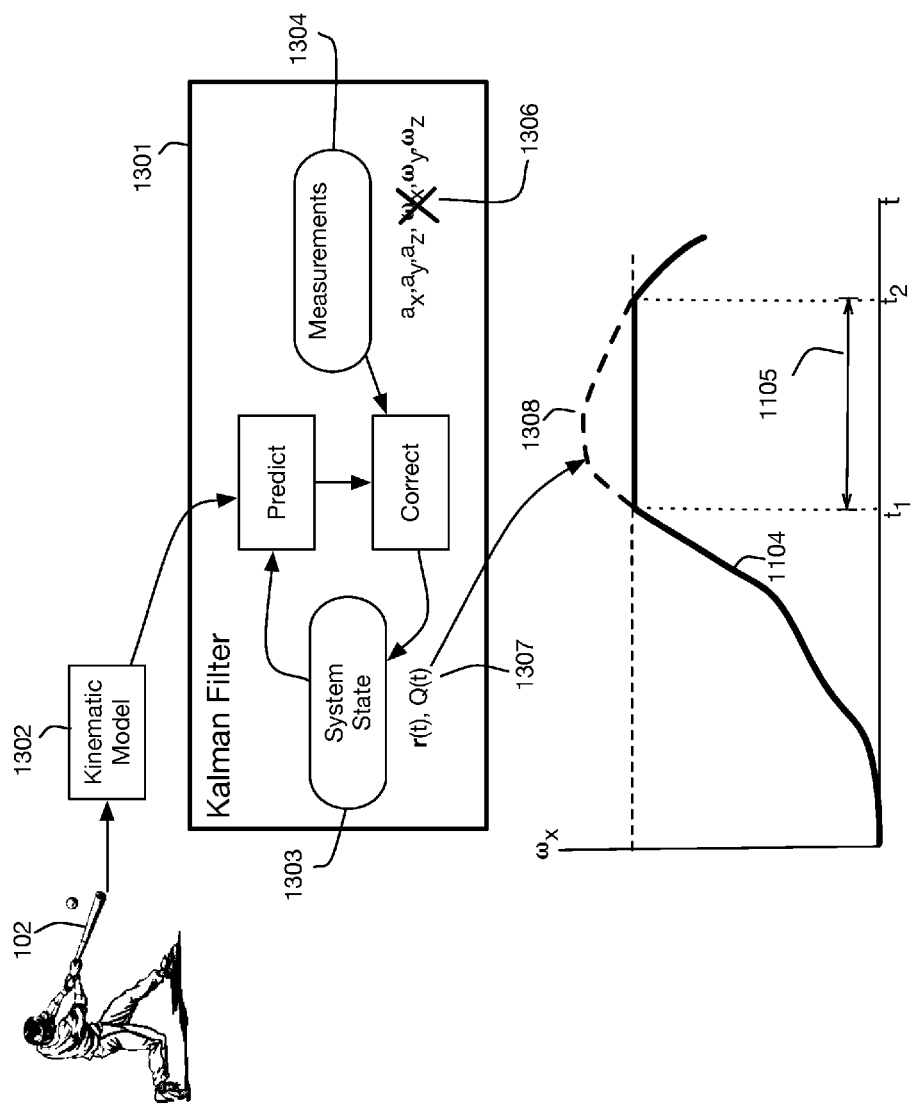
FIG. 13 illustrates an embodiment that extrapolates sensor data using a Kalman filter to estimate values when the measurement range of the sensor is exceeded.

Another approach to extrapolation that may be used in one or more embodiments is to use a Kalman filter (or a variation of a Kalman filter like an Extended Kalman Filter or an Unscented Kalman Filter). FIG. 13 illustrates an example that uses this approach. Kalman filter 1301 incorporates a kinematic model 1302 of the bat 102. The system state 1303 is estimated for each sample point, and this estimate is corrected based on measurements 1304. The state 1303 for example may include the position r(t) and the orientation Q(t) of the bat, and the measurements 1304 may include for example accelerometer values $a_x$, $a_y$, $a_z$ and gyroscope values $\omega_x$, $\omega_y$, $\omega_z$. During time intervals when one or more measurements are not available or are saturated, such as x-axis angular velocity 1306 during time interval 1105, the filter 1301 continues to predict state values 1303. Therefore, the curve 1104 can be extrapolated to curve 1308 through interval 1105; for example, the orientation 1307 may be differentiated to estimate the x-axis angular velocity 1308 in this interval.

In general, one or more embodiments may use a recursive state space estimator (e.g., Kalman filter) with a kinematic model of the physical body or equipment being measured. The state-space propagation model may be used to impose appropriate physical constraints. The state space estimate and its uncertainty (covariance) may be updated using the non-saturated measurements from the various sensors. An estimate of the missing (saturated) parameter may then be derived from the state space estimate. Likewise, the uncertainty in the estimated parameter may be derived from the model uncertainty. Either the state space propagation model or the measurement model (or both) may be non-linear, in which case a linearized (EKF) or sigma-point (UKF) filter may be used. Finally, the uncertainty in the extrapolated time series (or the state space estimate itself) may be propagated to derived metrics. For example, in a baseball swing like the swing illustrated in FIG. 13, the gyroscope may be saturated into impact, which affects the accuracy of the swing speed measurement. Using this approach, it is possible to estimate the actual swing speed and provide an uncertainty interval (error bars).

While the ideas herein disclosed has been described by means of specific embodiments and applications thereof, numerous modifications and variations could be made thereto by those skilled in the art without departing from the scope of the invention set forth in the claims.

What is claimed is:

1. A swing analysis method using a swing plane reference frame, comprising
obtaining sensor data from a sensor coupled to a piece of equipment or bat during a swing of said piece of equipment or bat by a user to hit or contact a ball, wherein said sensor comprises a processor;
determining a time of impact between said piece of equipment or bat and said ball from said sensor data via said processor;
calculating a trajectory during said swing from said sensor data via said processor, said trajectory comprising a time series of motion data samples, wherein each motion data sample of said motion data samples comprising one or more of
a position;
an orientation;
a velocity;
an angular velocity;
an acceleration; and,
an angular acceleration;
calculating an impact velocity vector from said trajectory as said velocity of said piece of equipment or bat at said time of impact via said processor;
defining a swing plane reference frame via said processor, wherein said swing plane reference plane comprising
a first axis defined by a longitudinal axis of said piece of equipment or bat at said time of impact;
a second axis defined by said impact velocity vector; and,
a third axis orthogonal to a swing plane spanned by said first axis and said second axis;
transforming said trajectory to said swing plane reference frame to form a swing plane frame trajectory via said processor;
analyzing said swing plane frame trajectory to create one or more swing metrics that describe said swing of said piece of equipment or bat by said user via said processor;
obtaining a database of swings from a plurality of players via said processor;
analyzing said database of swings to generate one or more performance rating functions that map said one or more swing metrics into a performance rating via said processor;
applying said one or more performance rating functions to said one or more swing metrics that describe said swing of said piece of equipment or bat by said user to determine a performance rating for said swing of said piece of equipment or bat by said user via said processor; and,
providing feedback to said user that comprises said performance rating for said swing of said piece of equipment or bat by said user via said processor.

2. The method of claim 1, wherein said sensor comprises a three axis accelerometer that generates acceleration data; and,
a three axis gyroscope that generates angular velocity data.

3. The method of claim 2, wherein said sensor further comprises
   a three axis magnetometer that generates magnetic field data.

4. The method of claim 1, wherein said sensor comprises a plurality of sensors located at different locations on said piece of equipment or bat.

5. The method of claim 1, wherein said sensor generates said sensor data at least ten times per second during said swing of said piece of equipment or bat.

6. The method of claim 1, wherein said sensor generates said sensor data at least one hundred times per second or more during said swing of said piece of equipment or bat.

7. The method of claim 1, wherein said bat comprises one or more of a baseball bat, a softball bat, and a cricket bat, or wherein said piece of equipment comprises one or more of a tennis racket, a table tennis racket, a badminton racket, a squash racket, a racquetball racket, a golf club, a polo mallet, a hockey stick, a field hockey stick, and a lacrosse stick.

8. The method of claim 1, further comprising
   calculating a time series of swing plane speed from said swing plane frame trajectory as a rotational speed component in said swing plane via said processor.

9. The method of claim 8, wherein said swing plane speed is a projection of said angular velocity onto said third axis orthogonal to said swing plane.

10. The method of claim 8, further comprising
    calculating a start of downswing time as a latest time prior to said time of impact when said swing plane speed has magnitude zero via said processor; and,
    calculating a time to contact metric as a difference between said time of impact and said start of downswing time via said processor.

11. The method of claim 10, further comprising
    calculating a total swing angle metric as a total angle traversed by said piece of equipment or bat in said swing plane between said start of downswing time and said time of impact via said processor; and,
    calculating an off plane angle metric as a total angle traversed by said piece of equipment or bat orthogonal to said swing plane between said start of downswing time and said time of impact via said processor.

12. The method of claim 8, further comprising
    calculating a peak speed metric as a maximum magnitude of said swing plane speed during said swing via said processor;
    calculating a halfway point in said swing via said processor; and,
    calculating a swing tempo metric as a ratio of said swing plane speed at said halfway point to said peak speed metric via said processor.

13. The method of claim 1, further comprising
    comparing said swing of said piece of equipment or bat by said user to said database of swings to identify one or more players from said plurality of players that have swings that are similar to said swing of said piece of equipment or bat by said user via said processor.

14. The method of claim 1, further comprising
    combining said one or more swing metrics into a swing feature vector via said processor; and,
    applying machine learning to said database of swings using said swing feature vector to classify each swing in said database of swings into a swing style that is based on said swing feature vector via said processor.

15. The method of claim 14, further comprising
    determining the swing style for said swing of said piece of equipment or bat by said user based on said swing feature vector for said swing of said piece of equipment or bat by said user via said processor.

16. The method of claim 1, further comprising
    when one or more sensor values of said sensor data are unavailable or are at a limit of a measurement range of said sensor during a time interval, extrapolating previous measurements or future measurements of said sensor to form an estimate of said one or more sensor values during said time interval via said processor.

17. The method of claim 16, wherein said extrapolating comprises generating a Bézier curve having control points based on said previous measurements or future measurements.

18. The method of claim 17, wherein
    said Bézier curve is a cubic Bézier curve having four control points;
    a first control point of said four control points is a point matching said previous measurements at a starting point of said time interval;
    a second control point of said four control points lies on a tangent to said previous measurements at said first control point;
    a fourth control point of said four control points is a point matching said future measurements at an ending point of said time interval; and,
    a third control point of said four control points lies on a tangent to said future measurements at said fourth control point.

19. The method of claim 16, wherein said extrapolating comprises using a Kalman filter to form said estimate of said one or more sensor values during said time interval, wherein said Kalman filter comprises a kinematic model of said piece of equipment or bat.

20. A swing analysis method using a swing plane reference frame, comprising
    obtaining sensor data from a sensor coupled to a piece of equipment or bat during a swing of said piece of equipment or bat by a user to hit or contact a ball, wherein said sensor comprises a processor;
    determining a time of impact between said piece of equipment or bat and said ball from said sensor data via said processor;
    calculating a trajectory during said swing from said sensor data via said processor, said trajectory comprising a time series of motion data samples, wherein each motion data sample of said motion data samples comprising one or more of
    a position;
    an orientation;
    a velocity;
    an angular velocity;
    an acceleration; and,
    an angular acceleration;
    calculating an impact velocity vector from said trajectory as said velocity of said piece of equipment or bat at said time of impact via said processor;
    defining a swing plane reference frame via said processor, wherein said swing plane reference plane comprising
    a first axis defined by a longitudinal axis of said piece of equipment or bat at said time of impact;
    a second axis defined by said impact velocity vector; and,
    a third axis orthogonal to a swing plane spanned by said first axis and said second axis;
    transforming said trajectory to said swing plane reference frame to form a swing plane frame trajectory via said processor; and, analyzing said swing plane frame trajectory to create one or more swing metrics that describe said swing of said piece of equipment or bat by said user via said processor;

when one or more sensor values of said sensor data are unavailable or are at a limit of a measurement range of said sensor during a time interval, extrapolating previous measurements or future measurements of said sensor to form an estimate of said one or more sensor values during said time interval via said processor.

21. The method of claim 20, wherein said extrapolating comprises generating a Bézier curve having control points based on said previous measurements or future measurements.

22. The method of claim 21, wherein said Bézier curve is a cubic Bézier curve having four control points;

a first control point of said four control points is a point matching said previous measurements at a starting point of said time interval;

a second control point of said four control points lies on a tangent to said previous measurements at said first control point;

a fourth control point of said four control points is a point matching said future measurements at an ending point of said time interval; and, a third control point of said four control points lies on a tangent to said future measurements at said fourth control point.

23. The method of claim 20, wherein said extrapolating comprises using a Kalman filter to form said estimate of said one or more sensor values during said time interval, wherein said Kalman filter comprises a kinematic model of said piece of equipment or bat.

* * * * *